United States Patent [19]
Rodan et al.

[11] Patent Number: 5,866,397
[45] Date of Patent: Feb. 2, 1999

[54] HUMAN PROTEIN TYROSINE PHOSPHATASE OB PROTEIN

[75] Inventors: Gideon A. Rodan, Bryn Mawr; Su Jane Rutledge, East Greenville; Azriel Schmidt, Bryn Mawr, all of Pa.

[73] Assignee: Merck & Co., Inc., Rahway, N.J.

[21] Appl. No.: 800,825

[22] Filed: Feb. 14, 1997

Related U.S. Application Data

[60] Division of Ser. No. 348,006, Dec. 1, 1994, Pat. No. 5,658,756, which is a continuation-in-part of Ser. No. 122,032, Sep. 14, 1993, abandoned.

[51] Int. Cl.[6] ............................. C12N 9/16; C12N 15/55
[52] U.S. Cl. .......................... 435/196; 435/69.1; 530/350
[58] Field of Search ................................... 435/69.1, 196; 530/350

[56] References Cited

PUBLICATIONS

Yi et al. "Identification of Novel Protein Tyrosine Phosphatases of Hematopoietic Cells by Polymerase Chain Reaction Amplification", Blood, vol. 78, No. 9, Nov. 1991; pp. 2222–2228.

Wergedal et al. "Human Bone Cells Contain a Fluoride Sensitive Acid Phosphatase: Evidence that this Enzyme Functions at Neutral pH as a Phosphotyrosyl Protein Phosphatase"; Clin. Biochem. vol. 25, Feb. 1992; pp. 47–53.

Kaplan et al. "Cloning of three human tyrosine phosphatases reveals a multigene family of receptor–linked protein–tyrosine–phosphatases expressed in brain", Proc. Natl. Acad. Sci., vol. 87, pp. 7000–7004, 1990.

Chernoff et al. "Cloning of a cDNA for a major human protein–tyrosine–phosphatase", Proc. Natl. Acad. Sci, vol. 87, pp. 2735–2739, Apr. 1990.

Krueger et al. "A human transmembrane protein tyrosine phosphatase, PTP, is expressed in bring and has an N–terminal receptor domain homologous to carbonic anhydrases", Proc. Natl. Acad. Sci., vol. 89, pp. 7417–7421, Aug. 1992.

Hashimoto et al. "Insulin receptor and epidermal growth factor receptor dephosphorylation by three major rat liver protein–tyrosine phosphatases expressed in a recombinant bacterial system", J. Biochem. vol. 284, (1992) pp. 569–572.

Lau et al. "Purification and Characterization of an Acid Phosphatase that Displays Phosphotyrosyl protein Phosphatase Activity from Bovine Cortical Bone Matrix", J. of Biol. Chem. vol. 262, No. 3, pp. 1389–1397, 1987.

Lau et al. "Phosphotyrosyl protein phosphatases", Biochem. (1989) vol. 257, pp. 23–26.

Mizuno et al. "Developmental regulation of gene expression for the MPTp isoforms in the central nervous system and the immune system", FEBS Letters 355 (1994) 223–228.

*Primary Examiner*—Sally P. Teng
*Attorney, Agent, or Firm*—J. Mark Hand; Jack L. Tribble

[57] ABSTRACT

A novel human protein tyrosine phosphatase (PTP) has been identified and its cDNA has been isolated. This novel PTP, denoted PTP-OB, has a receptor-like three dimensional structure and is present in osteoblasts. PTP-OB is involved in osteoblast differentiation, and modulators of PTP-OB activity in turn modulate osteoblast differentiation, osteoclast differentiation and osteoclast activity.

7 Claims, 12 Drawing Sheets

FIG. 11

```
  1  MEPFCPLLLA SFSLSLARAG QGNDTIPTES NWTSTTAGPP DPGASQPLLI
 51  WLLPLLLLL FLLAAYFFRF RKQRKAVVSS NDKKMPNGIL EEQEQQRVML
101  LSRSPSGPKK FFPIPVEHLE EEIRVRSADD CKRFREEFNS LPSGHIQGTF
151  ELANKEENRE KNRYPNILPN DHCRVILSQV DGIPCSDYIN ASYIDGYKEK
201  NKFIAAQGPK QETVNDFWRM VMEQRSATIV MLTNLKERKE EKCYQYWPDQ
251  GCWTYGNIRV CVEDCVVLVD YTIRKFCIHP QLPDSCKAPR LVSQLHFTSW
301  PDFGVPFTPI GMLKFLKKVK TLNPSHAGPI VVHCSAGVGR TGTFIVIDAM
351  MDMIHSEQKV DVFEFVSRIR NQRPQMVQTD VQYTFIYQAL LEYYLYGDTE
401  LDVSSLERHL QTLHSTATHF DKIGLEEEFR KLTNVRIMKE NMRTGNLPAN
451  MKKARVIQII PYDFNRVILS MKRGQEFTDY INASFIDGYR QKDYFMATQG
501  PLAHTVEDFW RMVWEWKSHT IVMLTEVQER EQDKCYQYWP TEGSVTHGDI
551  TIEIKSDTLS EAISVRDFLV TFKQPLARQE EQVRMVRQFH FHGWPEVGIP
601  AEGKGMIDLI AAVQKQQQQT GNHPITVHCS AGAGRTGTFI ALSNILERVK
651  AEGLLDVFQA VKSLRLQRPH MVQTLEQYEF CYKVVQDFID IFSDYANFK
                                                          699
                        (SEQ ID NO. 7)
```

HUMAN PROTEIN TYROSINE PHOSPHATASE OB PROTEIN

RELATED APPLICATIONS

This is a division of application Ser. No. 08/348,006, filed Dec. 1, 1994, now U.S. Pat. No. 5,658,756, which is a continuation-in-part application of application Ser. No. 08/122,032, filed 14 Sep., 1993, now abandoned.

BACKGROUND OF THE INVENTION

Protein tyrosine phosphorylation plays an important role in the regulation of cellular signal transduction, cell growth and differentiation. The level of tyrosine phosphorylation is controlled by the equilibrium of the activities of the protein tyrosine kinases (PTK) and protein tyrosine phosphatases (PTP) (Cantley, L. C. et al., 1991, Cell, 64, pp.281–302; Fischer, E. H. et al., 1991, Science, 253, pp.401–406; Alexander, D. R. and Cantrell, D. A., 1989, Immunol. Today, 10, pp.200–205; Tonks, N. K. and Charbonneau, H., 1989, Trends Biochem.Sci., 14, pp.497–500; Saito, H. and Streuli, M. 1991. Cell Growth And Differentiation, 2, pp.59–65; Gautier, J. et al., 1991, Cell, 67, pp.197–211; Zheng, X. M. et al., Nature, 359, pp.336–339). It is well documented that tyrosine kinase activities play an important role in the growth and the differentiation of bone cells. M-CSF and its receptor c-fms were shown to be crucial in osteoclast development. Recently Soriano et al. reported that disruption of c-src proto-oncogene, by homologous recombination, induced osteoporosis, that is characterized by the reduction of bone resorption due to impairment of osteoclastic function (Soriano, P. et al., 1991, Cell, 64, pp.693–702; Boyce, B. F. et al., 1992, J.Clin.Invest., 90, pp.1622–1627). In both in vivo and in vitro experiments it was demonstrated that FGF, IGF-I and IGF-II are important for the osteoblast functions. These findings suggest that the control of tyrosine phosphorylation is clearly important for bone cells.

As mentioned above, protein tyrosine phosphorylation is tightly balanced by the opposing actions of protein tyrosine kinases and protein tyrosine phosphatases. Treatment of bone cells with orthovanadate, a PTPase inhibitor, resulted in the stimulation of cell proliferation and the synthesis of bone collagen (Lau et al. Endocrinology, 1988, 123 pp. 2858–2867). In organ cultures, vanadate treatment inhibited the stimulation of bone resorption induced by treatment with PTH (Krieger and Tashjian, Endocrinology, 1983, 113, pp. 324–328). Taken together, these findings suggest that PTPases play an important function in bone cells.

SUMMARY OF THE DISCLOSURE

The polymerase chain reaction methodology was used to identify cDNA molecules for several PTPases in bone cells. One of these cDNA clones, named PTP-OB, encoded a novel member of the protein tyrosine phosphatase family. From human cDNA libraries, the entire open reading frame-encoding DNA was cloned for that protein. PTP-OB is composed of 1911 amino acid residues. Sequence analysis revealed two regions of hydrophobic amino acid residues that comprise a putative signal peptide and transmembrane domain, thus indicating PTP-OB as a receptor-like PTPase. The amino acid sequence of PTP-OB shows the best similarity to LAR and LAR related PTPases. As described for LAR, three immunoglobulin-like and eight fibronectin type III-like domains can be identified in the extracellular domain, and two tandem repeats of PTPase domains in the cytoplasmic region. The cDNA clones isolated from human brain library contained a deletion of 1227 bp that maintained the open reading frame, but coded for an extracellular region that was shorter by 409 amino acid residues and one with one amino acid substitution. Hybridization experiments revealed that PTP-OB was expressed as a 7.3 kilo base (kb) mRNA in both bone and brain tissues. The tissue distribution of PTP-OB transcript suggested that this receptor-like PTPase is involved in the growth and differentiation of osteoblasts and brain cells.

BRIEF DESCRIPTION OF THE DRAWINGS

FIG. 11 The amino acid sequence of the mouse mPTPε (SEQ ID NO:7) is and has the structure of a transmembrane protein; the signal peptide and transmembrane regions are underlined, and the conserved PTP regions are boxed.

DETAILED DESCRIPTION OF THE INVENTION

Figure 1:
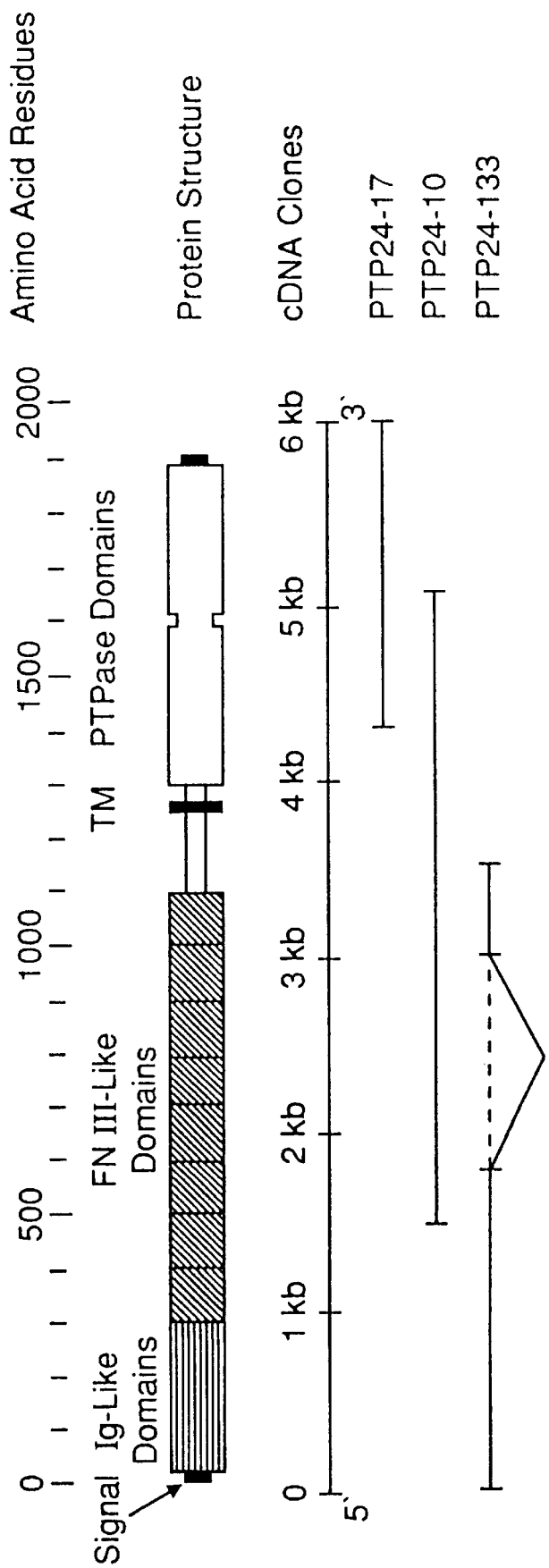
FIG. 1 Schematic structure of PTP-OB overlapping cDNA clones were isolated from various human cDNA libraries: PTP-OB-17 from human fetal lung library, PTP-OB-10 human giant cell tumor library and PTP-OB-133 from human fetal brain library are shown, depicting the extracellular region with the signal peptide, the immunoglobulin-like domains (Ig-like), the fibronectin (FN) type III-like domains, the transmembrane (TM) domain and the cytoplasmic region with the PTPase domains.

The present invention relates to cDNA encoding a novel protein tyrosine phosphatase termed PTP-OB. The present invention is also related to recombinant host cells which express the cloned PTP-OB-encoding DNA contained in a recombinant expression plasmid. The present invention is also related to a method for the screening of substances which modulate PTP-OB protein activity. The DNA of the present invention is isolated from PTP-OB producing cells. PTP-OB, as used herein, refers to a protein tyrosine phosphatase which is specifically expressed in bone and brain cells. The present invention also relates to a unique protein tyrosine phosphatase protein, also described as PTP-OB, which is isolated from PTP-OB producing cells. PTP-OB protein, as used herein, refers to a protein tyrosine phosphatase protein which is specifically produced by bone and brain cells.

Mammalian cells capable of producing PTP-OB include, but are not limited to, cells derived from bone such as MB1.8 and brain cells such as U340. Transformed mammalian cell lines which produce PTP-OB include, but are not limited to, NIH 3T3 cells. The preferred cells for the present invention include normal human HELA, NIH 3T3, U2, and CHO cells and the most preferred cells are human 293 cells.

Other cells and cell lines may also be suitable for use to isolate PTP-OB cDNA. Selection of suitable cells may be done by screening for PTP-OB produced by the cells. Methods for detecting PTP-OB activity are well known in the art (in: Maniatis, T., Fritsch, E. F., Sambrook, J., Molecular Cloning: A Laboratory Manual Cold Spring Harbor Laboratory, Cold Spring Harbor, N.Y., 1982) and measure the level of PTP-OB RNA produced by the cells. Cells which possess PTP-OB activity in this assay may be suitable for the isolation of PTP-OB cDNA.

Any of a variety of procedures may be used to clone PTP-OB cDNA. These methods include, but are not limited to, direct functional expression of the PTP-OB cDNA following the construction of an PTP-OB-containing cDNA library in an appropriate expression vector system. Another method is to screen an PTP-OB-containing cDNA library constructed in a bacteriophage or plasmid shuttle vector with a labelled oligonucleotide probe designed from the amino acid sequence of the PTP-OB protein. The preferred method consists of screening an PTP-OB-containing cDNA library constructed in a bacteriophage or plasmid shuttle vector with a partial cDNA encoding the PTP-OB protein. This partial cDNA is obtained by the specific PCR amplification of PTP-OB DNA fragments through the design of degenerate oligonucleotide primers from the amino acid sequence known for other PTP-OB-family protein tyrosine phosphatases which are related to the PTP-OB protein.

It is readily apparent to those skilled in the art that other types of libraries, as well as libraries constructed from other cells or cell types, may be useful for isolating PTP-OB-encoding DNA. Other types of libraries include, but are not limited to, cDNA libraries derived from other cells or cell lines other than human such as mouse or rat cells, and genomic DNA libraries.

It is readily apparent to those skilled in the art that suitable cDNA libraries may be prepared from cells or cell lines which have PTP-OB activity. The selection of cells or cell lines for use in preparing a cDNA library to isolate PTP-OB cDNA may be done by first measuring cell associated PTP-OB activity using the known assay cited above and used herein.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N.Y., 1982).

It is also readily apparent to those skilled in the art that DNA encoding PTP-OB may also be isolated from a suitable genomic DNA library.

Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual (Cold Spring Harbor Laboratory, Cold Spring Harbor, N.Y., 1982).

In order to clone the PTP-OB gene by one of the preferred methods, the amino acid sequence or DNA sequence of PTP-OB or a homologous protein may be necessary. To accomplish this, PTP-OB protein or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial PTP-OB DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the PTP-OB sequence but others in the set will be capable of hybridizing to PTP-OB DNA even in the presence of DNA oligonucleotides with mismatches. The mismatched DNA oligonucleotides may still sufficiently hybridize to the PTP-OB DNA to permit identification and isolation of PTP-OB encoding DNA.

Using one of the preferred methods, cDNA clones encoding PTP-OB are isolated in a two-stage approach employing polymerase chain reaction (PCR) based technology and cDNA library screening. In the first stage, $NH_2$-terminal and internal amino acid sequence information from the purified PTP-OB or a homologous protein is used to design degenerate oligonucleotide primers for the amplification of PTP-OB-specific DNA fragments. In the second stage, these fragments are cloned to serve as probes for the isolation of full length cDNA from a cDNA library derived from human osteosarcoma or brain cells.

The sequence for the near full-length cDNA encoding PTP-OB is shown in SEQ ID NO:6, and was designated clone PTP-OB. The deduced amino acid sequence of PTP-OB from the cloned cDNA is shown in SEQ ID NO:5. Inspection of the determined cDNA sequence reveals the presence of a single, large open reading frame that encodes for an approximately 1911 amino acid protein.

The cloned PTP-OB cDNA obtained through the methods described above may be recombinantly expressed by molecular cloning into an expression vector containing a suitable promoter and other appropriate transcription regulatory elements, and transferred into prokaryotic or eukaryotic host cells to produce recombinant PTP-OB. Techniques for such manipulations can be found described in Maniatis, T, et al., supra, and are well known in the art.

Expression vectors are defined herein as DNA sequences that are required for the transcription of cloned DNA and the translation of their mRNAs in an appropriate host. Such vectors can be used to express eukaryotic DNA in a variety of hosts such as bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant PTP-OB in mammalian cells. Commercially available mammalian expression vectors which may be suitable for recombinant PTP-OB expression, include but are not limited to, pMC1neo (Stratagene), pXT1 (Stratagene), pSG5 (Stratagene), pcDNAI, pcDNAIamp (Invitrogen), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565)

DNA encoding PTP-OB may also be cloned into an expression vector for expression in a host cell. Host cells may be prokaryotic or eukaryotic, including but not limited to bacteria, yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, protoplast fusion, and electroporation. The expression vector-containing cells are individually analyzed to determine whether they produce PTP-OB protein. Identification of PTP-OB expressing cells may be done by several means, including but not limited to immunological reactivity with anti-PTP-OB antibodies, and the presence of host cell-associated PTP-OB activity.

Expression of PTP-OB DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the PTP-OB cDNA sequence(s) that yields optimal levels of PTP-OB protein, PTP-OB cDNA molecules including but not limited to the following can be constructed: the full-length open reading frame of the PTP-OB cDNA and various constructs containing portions of the cDNA encoding only specific domains of the protein or rearranged domains of the protein. All constructs can be designed to contain none, all or portions of the 5' and/or 3' untranslated region of PTP-OB cDNA. PTP-OB activity and levels of protein expression can be determined following the introduction, both singly and in combination, of these constructs into appropriate host cells. Following determination of the PTP-OB cDNA cassette yielding optimal expression in transient assays, this PTP-OB cDNA construct is transferred to a variety of expression vectors (including recombinant viruses), including but not limited to those for mammalian cells, plant cells, insect cells, oocytes, bacteria, and yeast cells.

Levels of PTP-OB protein in host cells is quantitated by a variety of techniques including, but not limited to, immunoaffinity and/or ligand affinity techniques. PTP-OB-specific affinity beads or PTP-OB-specific antibodies are used to isolate $^{35}$S-methionine labelled or unlabelled PTP-OB protein. Labelled PTP-OB protein is analyzed by SDS-PAGE. Unlabelled PTP-OB protein is detected by Western blotting, ELISA or RIA assays employing PTP-OB specific antibodies.

Following expression of PTP-OB in a host cell, PTP-OB protein may be recovered to provide PTP-OB in active form. Several PTP-OB purification procedures are available and suitable for use. Recombinant PTP-OB may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant PTP-OB can be separated from other cellular proteins by use of an immuno-affinity column made with monoclonal or polyclonal antibodies specific for full length PTP-OB, or polypeptide fragments of PTP-OB.

Monospecific antibodies to PTP-OB are purified from mammalian antisera containing antibodies reactive against PTP-OB or are prepared as monoclonal antibodies reactive with PTP-OB using the technique of Kohler and Milstein, Nature 256: 495–497 (1975). Monospecific antibody as used herein is defined as a single antibody species or multiple antibody species with homogenous binding characteristics for PTP-OB. Homogenous binding as used herein refers to the ability of the antibody species to bind to a specific antigen or epitope, such as those associated with the PTP-OB, as described above. PTP-OB specific antibodies are raised by immunizing animals such as mice, rats, guinea pigs, rabbits, goats, horses and the like, with an appropriate concentration of PTP-OB either with or without an immune adjuvant.

Preimmune serum is collected prior to the first immunization. Each animal receives between about 0.1 μg and about 1000 μg of PTP-OB associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of the PTP-OB protein in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunizaiton. Those animals receiving booster injections are generally given an equal amount of PTP-OB in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with PTP-OB are prepared by immunizing inbred mice, preferably Balb/c, with PTP-OB. The mice are immunized by the IP or SC route with about 1 μg to about 100 μg, preferably about 10 μg, of PTP-OB in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 μg of PTP-OB in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using PTP-OB as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about 2×10⁶ to about 6×10⁶ hybridoma cells about 4 days after priming. Ascites fluid is collected at approximately 8–12 days after cell transfer and the monoclonal antibodies are purified by techniques known in the art.

In vitro production of anti-PTP-OB mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of PTP-OB in body fluids or tissue and cell extracts.

It is readily apparent to those skilled in the art that the above described methods for producing monospecific antibodies may be utilized to produce antibodies specific for PTP-OB polypeptide fragments, or full-length PTP-OB polypeptide.

PTP-OB antibody affinity columns are made by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) and the cell culture supernatants or cell extracts containing PTP-OB or PTP-OB fragments are slowly passed through the column. The column is then washed with phosphate buffered saline until the optical density ($A_{280}$) falls to background, then the protein is eluted with 0.23M glycine-HCl (pH 2.6). The purified PTP-OB protein is then dialyzed against phosphate buffered saline.

The novel PTP-OB protein tyrosine phosphatase of the present invention is suitable for use in an assay procedure for the identification of compounds which modulate the PTP-OB activity. Modulating PTP-OB activity, as described herein includes the inhibition or activation of the protein and also includes directly or indirectly affecting the normal regulation of the PTP-OB activity. Compounds which modulate the PTP-OB activity include agonists, antagonists, inhibitors, activators, and compounds which directly or indirectly affect regulation of the PTP-OB activity.

The PTP-OB protein tyrosine phosphatase of the present invention may be obtained from both native and recombinant sources for use in an assay procedure to identify PTP-OB modulators. In general, an assay procedure to identify PTP-OB modulators will contain the PTP-OB-protein of the present invention, and a test compound or sample which contains a putative PTP-OB modulator. The test compounds or samples may be tested directly on, for example, purified PTP-OB protein whether native or recombinant, subcellular fractions of PTP-OB-producing cells whether native or recombinant, and/or whole cells expressing the PTP-OB whether native or recombinant. The test compound or sample may be added to the PTP-OB in the presence or absence of a known PTP-OB modulator. The modulating activity of the test compound or sample may be determined by, for example, analyzing the ability of the test compound or sample to bind to PTP-OB protein, activate the protein, inhibit PTP-OB activity, inhibit or enhance the binding of other compounds to the PTP-OB protein, modifying receptor regulation, or modifying an intracellular activity.

The identification of modulators of PTP-OB activity are useful in treating disease states involving the PTP-OB activity such as osteoporosis. Other compounds may be useful for stimulating or inhibiting activity of the enzyme. These compounds are useful for the prevention and treatment of bone loss and the stimulation of bone formation. Such compounds could be of use in the treatment of diseases in which activation or inactivation of the PTP-OB protein results in either cellular proliferation, cell death, nonproliferation, induction of cellular neoplastic transformations or metastatic tumor growth and hence could be used in the prevention and/or treatment of cancers such as lung cancer and osteosarcoma. The isolation and purification of an PTP-OB-encoding DNA molecule would be useful for establishing the tissue distribution of PTP-OB as well as establishing a process for identifying compounds which modulate PTP-OB activity.

Isolated and purified PTP-OB DNA would also be useful for the recombinant production of large quantities of PTP-OB protein. The ability to produce large quantities of the protein would be useful for the production of a therapeutic agent comprising PTP-OB protein. A therapeutic agent comprised of PTP-OB protein would be useful in the treatment of PTP-OB-related diseases or conditions which are PTP-OB responsive.

By molecular cloning and DNA sequencing a new member of the protein tyrosine phosphates gene family, termed PTP-OB, was identified. PTP-OB has a receptor like structure and has the characteristic cytoplasmic protein tyrosine phosphatase region. The protein is composed of 1911 amino acid residues and shares similarities to the tyrosine phosphatases LAR, PTPδ and other known LAR related PTPases. Sequence analysis revealed two highly hydrophobic regions in PTP-OB protein. One, located at the amino terminus end, is likely to be the signal peptide. The second highly hydrophobic segment that is followed by positively charged residues is likely to serve as a transmembrane domain. In the cytoplasmic region, PTP-OB contains two tandem PTPase-like domains that are found in PTPase family. Sequence comparison with the known PTPases demonstrated that PTP-OB is homologues to LAR and PTPδ (Streuli, M. et al., 1988, J.Exp.Med., 168, pp.1523–1530; Krueger, N. X. et al., 1990, EMBO J., 9, pp.3241–3252). The overall amino acid sequence homology approaches 68% and 59% respectively. Although the primary amino acid of extracellular regions diverged from that of LAR, the extracellular region of PTP-OB was observed to contain the three Ig-like domains and eight fibronectin type-III like domains that were found in LAR (Streuli, M. supra).

Northern hybridization experiments with RNA from various cell and tissues indicated that both PTP-OB and PTPδ were expressed in bone and brain derived cells or tissues. Relatively high levels of PTP-OB and PTPδ transcripts were found in RNA isolated from human osteosarcoma tumor, human giant cell tumor, rat tibia and in relatively mature cultured osteoblasts isolated from mouse calvaria. Since osteosarcoma tumor is abundant with osteoblastic cells, and giant cell tumor is a mixed cell population of multinucleated osteoclast-like cells and osteoblastic cells and other non defmed cells, it is likely that in bone, the osteoblastic cells were the source of PTP-OB and PTPδ RNA. In addition to the expression in bone RNA encoding PTP-OB and PTPδ were found in human brain as well in RNA isolated from the human glioblastoma tumor cell line U340. Overall, the expression of PTP-OB was more restricted to brain or bone derived cells and tissues than that of PTPδ. In addition to the expression in brain and bone, low levels of PTPδ were found in RNA isolated from lung, liver, kidney and pancreas. Although the complete sequence of PTPδ is not known, from the available sequences, it appeared to be structurally related to LAR and to PTP-OB. Studies with the similar PTPases in drosophila, suggested that these receptor-like PTPases that share structural features with cell adhesion molecules are involved with cell to cell or cell to matrix interactions. For both brain and bone, cell to cell or cell to matrix contacts are continually modified in an ongoing process. In bone, these receptor-like PTPases, may regulate the interaction of osteoblasts with each other or with the bone matrix. Experiments with cultured osteoblats, showed that vanadate, a PTPase inhibitor, stimulated cell proliferation and the synthesis of bone collagen (Lau et aL supra). These findings, suggest that these PTPases may play an important function in osteoblasts and their exact functions are yet to be determined.

Mouse bone marrow cells are induced to differentiate into osteoclast-like cells by co-culture with neonatal calvaria osteoblasts, in the presence of 1,25(OH)$_2$D$_3$. These cells can resorb bone and exhibit markers, such as TRAP positive staining, calcitonin receptors and vitronectin receptors, that are associated with osteoclasts. Furthermore, like primary osteoclasts, the cells contain multiple nuclei as a result of cell fusion [Takahashi, N. T., N. Akastu, . Udagawa, T. Sasaki, A. Yamaguchi, J. M. Mosley, T. J. Martin, and T. Suda. 1988. Osteoblastic cells are involved in osteoclast formation. *Endocrinology* 123:2600–2602]. TRAP positive cells produced in the co-culture of osteoblasts and bone marrow cells can be recognized starting at four days of co-culture. The majority of the multinucleated osteoclast-like cells (70–80%) appear after six to seven days.

To identify the PTPs expressed in osteoclasts, a cDNA library prepared from the in vitro-generated mouse osteoclasts was screened under non-stringent hybridization conditions. A cDNA fragment that codes for the amino acid residues of the cytoplasmic region of PTPα was used as probe [Kaplan, R., B. Morse, K. Huebner, C. Croce, R. Howk, M. Ravera, G. Ricca, M. Jaye, and J. Schlessinger. 1990. Cloning of three human tyrosine phosphatases reveals a multigene family of receptor-linked protein-tyrosine-phosphatases expressed in brain. *Proc. Natl. Acad. Sci. USA* 87:7000–7004; Sap, J., P. D'Eustachio, D. Givol, and J. Schlessinger. 1990. Cloning and expression of a widely expressed receptor tyrosine phosphatase. *Proc. Natl. Acad. Sci. USA* 87:6112–6116; Matthews, R. J., E. D. Cahir, and M. L. Thomas. 1990. Identification of an additional member of the protein-tyrosine-phosphatase family: evidence for alternative splicing in the tyrosine phosphatase domain. *Proc. Natl. Acad. Sci. USA*. 87:4444–4448; Krueger, N. X., M. Streuli, and H. Saito. 1990. Structural diversity and evolution of human receptor-like protein tyrosine phosphatases. *EMBO J*. 9:3241–3252]. Several positive clones were obtained, and were analyzed by restriction enzyme digestion and cDNA sequencing. It was found that in addition to the cDNA for mouse PTPα, many clones were obtained that coded for a different PTP similar to the subsequently published human hPTPε, cloned from a cDNA library of human placenta [Krueger et al., supra]. We consider this to be the cDNA of mouse PTPε (mPTPε).

Sequence analysis revealed that the mouse mPTPε is composed of 699 amino acid residues and has the structure of a transmembrane protein (FIG. 11 [SEQ ID NO:7]). A putative signal peptide is located next to the translation start site and a hydrophobic region between amino acid residues 47 to 70 is most likely a transmembrane domain. Similar to the hPTPε, the mPTPε contains a cytoplasmic region with two tandem catalytic domains and a relatively short extracellular domain of 45–47 amino acid residues. In the putative mature protein, the extracellular region would be of 25 to 27 amino acid residues with two potential N-glycosylation sites. As indicated for hPTPε, no stop codon precedes the first codon for methionine, therefore it is noteworthy that although the 5' untranslated sequences of hPTPε and mPTPε are different, the putative translation start site of mPTPε is identical to that of hPTPε. Overall, the mPTPε and the hPTPε share 93% of the amino acid residues; most of the sequence differences are concentrated in the putative extracellular regions. Compared to human PTPε (SEQ ID NO:7), the mouse PTPε has a few amino acid substitutions, a deletion of two amino acids in the transmembrane domain and an additional amino acid residue in the short extracellular region.

Tissue distribution of PTPε expression. Hybridization of mPTPε cDNA to the mRNA isolated from enriched populations of in vitro differentiated osteoclastic cells revealed a major transcript of about 5 kb and a minor transcript of about 2 kb. Hybridization of mPTPε cDNA to mRNA isolated from rat tissues, including spleen, uterus, intestine, brain, muscle, bone (tibia), lung, ovary, liver, kidney and heart did not reveal any PTPε transcripts. In similar hybridization experiments, no PTPε transcripts in mRNA isolated from the following human tissues were detected: brain, placenta, lung, liver, skeletal muscle, kidney, and pancreas. To further test whether PTPε is expressed in osteoclasts from other species, we tested the expression of PTPε in a human giant cell tumor (osteoclastoma) and in an in vitro generated chicken osteoclast preparation, both highly enriched in multinucleated osteoclastic cells. PTPε transcripts were present in RNA from both sources. No expression of PTPε was found in osteosarcoma tumors that do not contain osteoclasts, or in RNA isolated from granulomatous tissue that is rich in other cell types.

To study the potential role of PTPε in osteoclasts, we followed the expression of PTPε during osteoclast differentiation. Total RNA was isolated from 1,25(OH)$_2$D$_3$-treated co-cultures of bone marrow and from osteoblastic mouse calvaria cells at various time points, and the expression of PTPε was assessed by Northern hybridization. We found that PTPε expression correlated with osteoclast differentiation. PTPε mRNA was first detected at four days of co-culture and increased thereafter to reach maximal expression at six days, when the number of osteoclastic cells peaked. No PTPε mRNA transcripts were detected when 1,25(OH)$_2$D$_3$ (10 nM) was omitted from the co-culture or when osteoblasts were cultured alone, with or without 1,25(OH)$_2$D$_3$. The PTPε mRNA was enriched several-fold in RNA prepared from enriched osteoclasts. These observations indicate that the RNA for PTPε originated from the osteoclasts and not from the osteoblasts.

Since PTPα has a widespread tissue distribution, and is very similar to PTPε, we tested the expression of this PTP in the co-cultured cells. Hybridization with the PTPα cDNA to the same filters showed that PTPα mRNA was constitutively expressed and did not change during the co-culture period. The PTPα RNA was present in both the cultured osteoblasts and the co-cultured cells and was not dependent on the presence of 1,25(OH)$_2$D$_3$. The level of PTPα transcripts was lower in RNA isolated from the enriched osteoclasts, which could be due to osteoblast contamination or lower levels of PTPα in osteoclastic cells.

The following examples are provided as illustrative of the present invention without, however, limiting the same thereto.

EXAMPLE 1
Primer Design

Degenerate DNA primers were designed to recognize the coding region of the conserved amino acid residues of a typical protein tyrosine phosphatase domain. The sense primer, PH4, was the degenerate oligomer, 5' CTTCTAGAA (A/G)TG(T/C)GC(G/T/C/A)CA(A/G)TA(T/C)TGGCC (SEQ.ID.NO.: 1), that was prepared according to the conserved amino acid residues Lys Cys Ala Glr Tyr Trp Pro (SEQ.ID.NO.: 2). The antisense primer, PH2a, 5'. GAAGCTTCC(C/A)A(C/T)(G/C/T/A/)CCTGCAC(T/A) (A/G)CA(G/A) TG(C/G/T/A)AC (SEQ.ID.NO.: 3), was designed to complement the DNA sequences coding for the amino acid residues Val His Cys Ser Ala Gly Val Gly (SEQ.ID.NO.: 4) of the tyrosine phosphatase domain.

cDNA Amplification

Single stranded randomly primed cDNA was prepared with the Mo-MLV reverse transcriptase (BRL) from RNA isolated from a human osteosarcoma Saos-2/B10 cells. The cDNA reaction (25 μl) was diluted into 300 μl water and heat denatured at 95° C. for 5 minutes and quickly chilled on ice. The cDNA (5 μl) and the above primer pair, PH2a and PH4 (0.5 μM each) were employed in the amplification reaction with the Amplitaq kit and the DNA thermal cycler (Perkin Elmer, Cetus). The amplification cycles were as follows: denaturation at 94° C., 70 seconds; annealing at 50° C. for 135 seconds; 3 minutes of gradual increase of the temperature to 72° C.; extension at 72° C., 4 minutes for 40 cycles. The amplified fragments were separated by electrophoresis on 5% polyacrylamide gel, cloned into plasmids and sequenced. The cDNA clones were than used to screen lamda gt11 cDNA libraries and positive clones were isolated and their two DNA strands were sequenced.

Screening of cDNA Libraries

The cDNA libraries of human fetal lungs that were prepared from a mixture of 19-week and 21-week-old fetuses and the human fetal brain of a 26-week-old male fetus were purchased (Clontech, CA). The human giant cell tumor and the human U340 brain tumor cell cDNA libraries were constructed in lamda gt11 by using a mixture of oligo dT and random primers (Super Script Choice System, BRL, MD). The cDNA libraries were plated at a density of 30,000 plaques per 150-mm plate and transferred to nylon filters (Hybond N, Amersham). A half or one million of recombinants of each library were screened using 32P-labeled probe. Positive plaques were identified and selected clones were inserted into plasmids and sequenced.

Cloning of PTP-OB cDNA

The polymerase chain reaction (PCR) strategy was employed in order to identify the PTPases that are expressed in bone-derived cells. Total RNA was isolated from human osteosarcoma SAOS-2/B10 cells after six of hours treatment with TPA or a control solution. The cDNA was prepared and subjected to PCR amplification with DNA primers that were synthesized according to the conserved amino acid residues of the tyrosine phosphatase domain found in the members of the PTP family. After separation of the amplification products on 5% polyacrylamide gel, multiple DNA fragments, with the size range of 290–315 bp, were observed with the reaction that contained the cDNA of the TPA treated cells. No detectable hybridizing DNA fragments were observed when the cDNA from the control cells was used as template. The DNA fragments were cloned into plasmid vectors and sequenced in their entirety. After sequence analysis, we found that the various cDNA clones represented DNA fragments of five different PTPases. Four of these PTPases were the known PTPδ (Krueger et al, 1990 EMBO J 9:3241–3252), PTPgamma (Sap et al, 1990, Proc.Natl.Acad.Sci. USA, 87, pp.6112–6116; Kaplan et al., 1990. Proc. Natl.Acad.Sci. USA 87:7000–7004), PTPalpha (Matthews et al., 1990, Proc.Natl.Acad.Sci. USA, 89, pp.2980–2984; Kaplan et al., supra), and PTP MEG (Gu, M. et al., 1992, Proc.Natl.Acad.Sci. USA, 89, pp.2980–2984). The fifth clone, named PTP-OB, is a novel, yet unreported, PTPase gene product.

To obtain a complete cDNA sequence for the human PTP-OB, several cDNA libraries were screened which were either purchased or prepared according to standard methods. From a human fetal lung library, three cDNA clones were obtained that hybridized with the amplified 283 bp DNA fragment of PTP-OB. Analysis of the DNA sequence revealed that these three clones were identical and their sequences matched that of PTP-OB. Complete DNA sequencing of clone PTP-OB-17, revealed a 1714 bp cDNA that contained an open reading frame coding for a PTP like protein that was interrupted by a putative termination codon (FIG. 1).

To find additional cDNA sequences, we screened the cDNA library of the giant cell tumor with the cDNA of PTP-OB-17. Seven cDNA clones were identified and the longest cDNA, PTP-OB-10, was analyzed. Sequence analysis revealed a 3613 bp open reading frame that encodes for 1204 amino acid residues (FIG. 1). Since the expression of PTP-OB was found in brain tissue a human brain cDNA library was screened with the 350 bp DNA fragment that corresponded to the most 5' end of clone PTP-OB-10. Sixty positive clones were identified and after size selection and partial sequencing of several lambda clones, a clone of 3588 bp was identified, PTP-OB-133, that contained an open reading frame that starts with the putative initiation codon at the 5' end. Overall, analysis of the assembled cDNA sequences revealed a cDNA of 5988 nucleotides that contained a long open reading frame of 5733 bp that codes for 1911 amino acid residues. At the 5' end of the cDNA three initiation codons were identified. The first methionine codon is the most suitable translation start site. A comparison of PTP-OB protein the known PTPases showed that it is most similar to PTPases LAR and LAR related PTPases. The amino acid sequence of PTP-OB showed 68% identity with LAR and 59% with PTPδ. Similar to LAR, PTP-OB has a receptor-like structure. A highly hydrophobic region is located next to the putative initiation codon, and is probably the signal peptide. According to the consensus rules for signal peptide cleavage, the thirtieth amino acid residue is probably the first amino acid of the mature protein. A second highly hydrophobic domain is found between amino acid residues 1253 to 1277 and is most likely to function as the transmembrane domain. Similar to observations for LAR, analysis of the primary amino acid sequence of the putative extracellular region indicated three repeats of immunoglobulin-like domains and eight fibronectin type III-like repeats (Streuli et al 1998). According to the consensus glycosylation sites, three potential N-linked glycosylation sites at position 250, 721 and 919 were identified. The extracellular domain of PTP-OB is 58% identical to the parallel domain of LAR and 40% identical to DLAR and is closely related to other LAR related PTPase proteins.

The cytoplasmic domain of PTP-OB is composed of 626 amino acid residues. In this region the two tandem repeats of protein tyrosine phosphatase domains are recognized. The cytoplasmic region is highly conserved and it is 95% and 87% identical to the parallel domains of LAR and PTPδ respectively.

Comparing the overlapping sequences of PTP-OB-10 and PTP-OB-133 revealed that the clone isolated from the brain library contained a deletion of 1225 nucleotides, between 1828–3055 of the complete sequence, that maintained the open reading frame. Partial analysis of several other clones obtained from the brain library, revealed that they all had similar deletions thus coding for a protein with an extracellular domain that is shorter by 409 amino acid residues (between residues 604–1013) and with a substitution of a valine residue, V1014, to an isoleucine residue, i1014.

EXAMPLE 2

Tissue Distribution Of PTP-OB Expression
RNA Hybridization

RNA was isolated by the modified guanidinium hydrochloride method or by guanidinium isothiocyanate method. Total RNA (20–30 μg) and polyA selected RNA (2–5 μg) were separated on formaldehyde agarose gels and transferred nylon filters and subjected to hybridization with (Hybond N, Amersham). A Northern blot of polyA+ RNA of various human tissues was purchased from Clontech, CA. The hybridization solutions contained 40–50% formamide (Hybrisol I and II, Oncor). After hybridization, the filters were washed in a solution of 2×SSC containing 0.1% SDS, and finally in 0.2×SSC/0.1% SDS solution at 55° C., and exposed to X-ray film (XAR-2, Kodak) with intensifying screen at −70° C. for up to 10 days.

Preparation of RNA and Hybridization. Rat tibiae were dissected free of soft tissue and the bone marrow was removed from the bones. RNA was isolated from these bones by the modified guanidinium hydrochloride method [Nemeth, G. G., A. Heydemann, and M. E. Bolander. 1989. Isolation and analysis of ribonucleic acids from skeletal tissues. *Anal. Biochem.* 183:301–304] and the guanidinium isothiocyanate method [Kaplan, R., B. Morse, K. Huebner, C. Croce, R. Howk, M. Ravera, G. Ricca, M. Jaye, and J. Schlessinger. 1990. Cloning of three human tyrosine phosphatases reveals a multigene family of receptor-linked protein-tyrosine-phosphatases expressed in brain. *Proc. Natl. Acad. Sci. USA* 87:7000–7004]. Total RNA (20–30 μg) or polyA+ selected RNA (2–5 μg) were electrophoresed on formaldehyde-containing agarose gels and transferred to nylon filters (Hybond N, Amersham). A poly A+ RNA blot of various human tissues was purchased from Clontech, CA. Poly A+ RNA from cultured chicken osteoclasts was also prepared. The hybridization solutions contained 40–50% formamide (Hybrisol I and II, Oncor, MD). After hybridization, the filters were washed in a solution of 2×SSC/0.1% SDS, and finally in 0.2×SSC/0.1% SDS solution at 55° C., and exposed to X-ray film (XAR-2, Kodak) with an intensifying screen at −70° C.

Expression of PTP-OB mRNA

Figure 2:
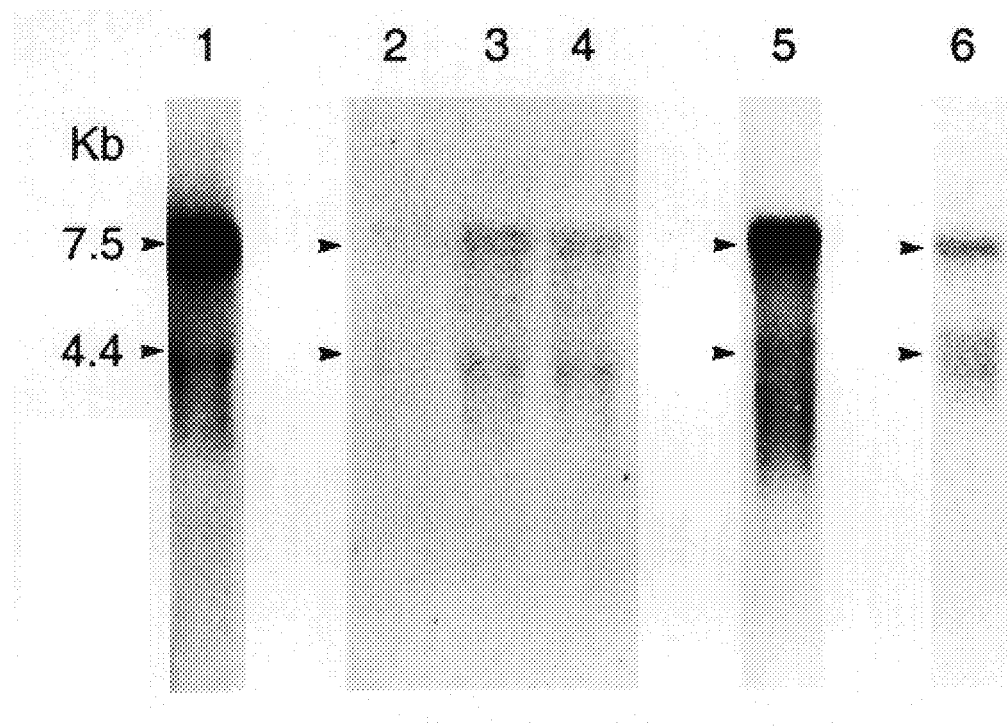
FIG. 2 Northern blots of RNA from human osteosarcoma (lane 1), human giant cell tumors (lanes 2–5), and rat tibia (lane 6) cells is shown.
Figure 3:
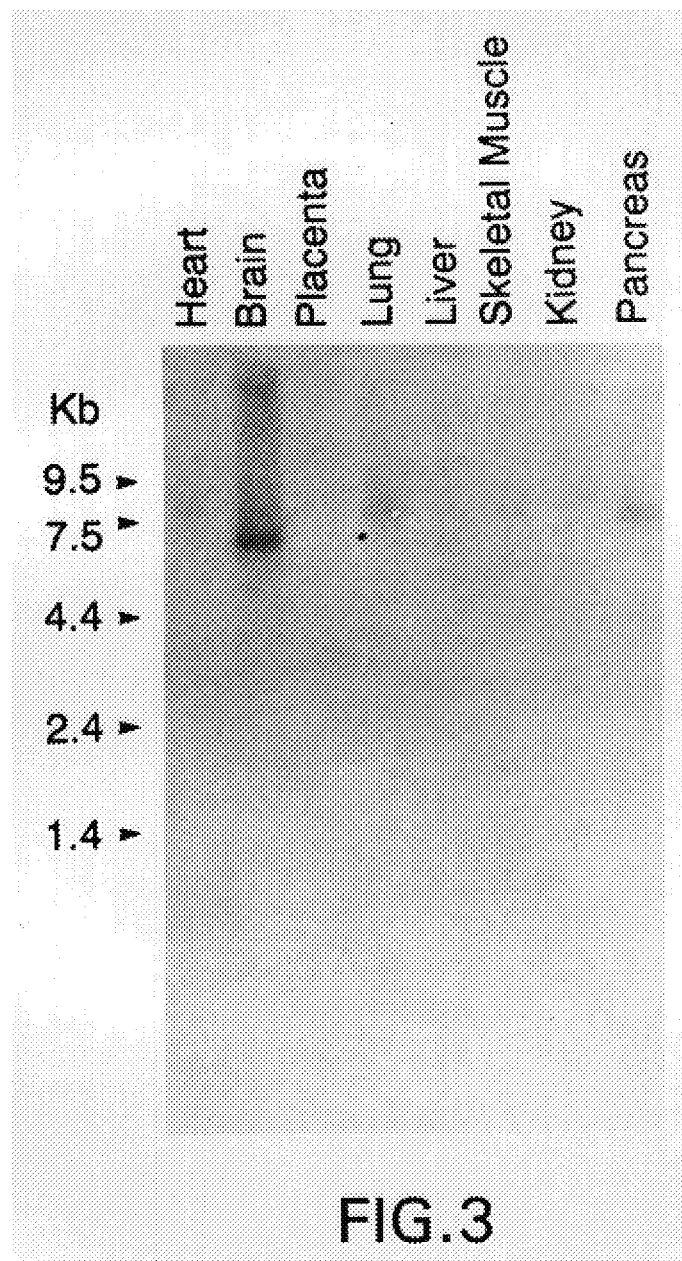
FIG. 3 A Northern blot of RNA from human tissues is shown.

PTP-OB cDNA was hybridized to RNA isolated from various cells and tissues. Northern hybridization experiments revealed that mRNA for PTP-OB is approximately 7.3 Kb. High steady state levels of PTP-OB RNA were found in human osteosarcoma tumor, giant cell tumor (GCT), and in mRNA prepared from human brain (FIGS. 2 and 3). In rat tissues, high level of expression of PTP-OB RNA was found in RNA prepared from tibia. Very low expression levels were detected in RNA isolated form lungs of one week old rat.

Figure 4:
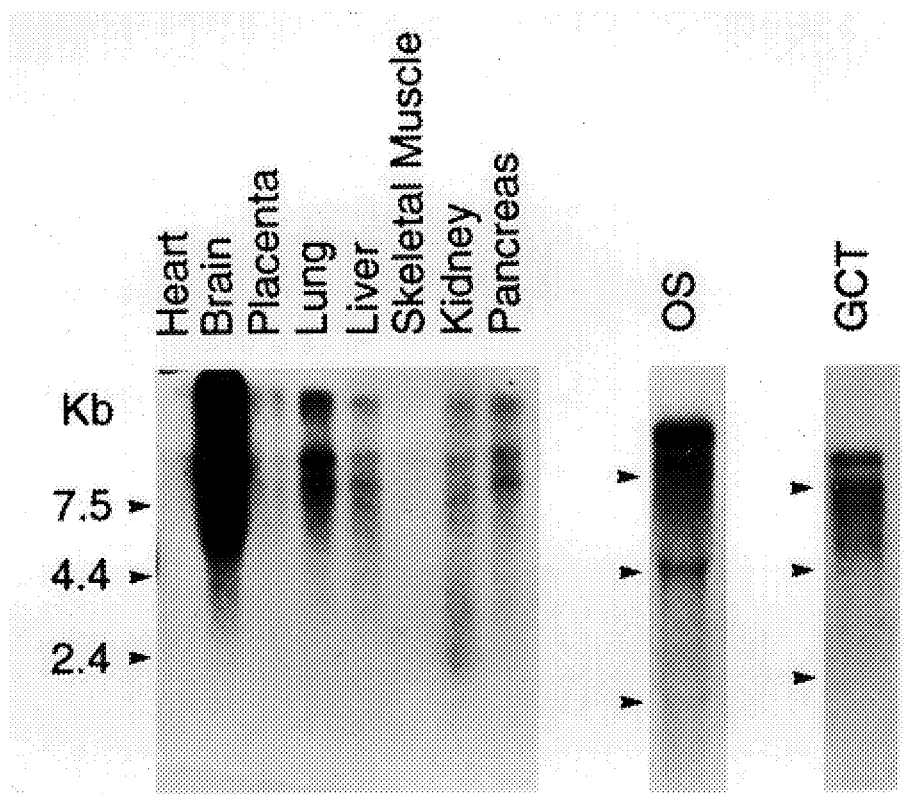
FIG. 4 Northern blots of RNA from human tissues is shown on the left, and of RNA from human tumor tissue on the right two lanes: osteosarcoma (OS) and giant cell tumor (GCT).

Hybridization experiments with the cDNA for PTPδ, showed tissue distribution that was comparable to PTP-OB. PTPδ was found to be highly expressed in brain. Lower levels of PTPδ transcripts were found in RNA isolated from lung and very low but detectable levels were observed in liver, kidney and pancreas. In bone derived cells, high expression levels of PTPδ was found in the human osteosarcoma tumor, and human giant cell tumor (FIG. 4). In cultured cells, there were high expression levels of both PTP-OB and PTPδ in osteoblasts isolated from mouse calvaria and in the human glioblastoma brain tumor U340.

EXAMPLE 3

Cloning of the PTP-OB cDNA into *E. coli* Expression Vectors

Recombinant PTP-OB is produced in *E. coli* following the transfer of the PTP-OB encoding DNA into *E. coli* expression vectors, including but not limited to, the pET series (Novagen). The pET vectors place PTP-OB expression under control of the tightly regulated bacteriophage T7 promoter. Following transfer of this construct into an *E. coli* host which contains a chromosomal copy of the T7 RNA polymerase gene driven by the inducible lac promoter, expression of PTP-OB is induced when an appropriate lac substrate (IPTG) is added to the culture. The levels of expressed PTP-OB are determined by the assays described above.

The cDNA encoding the entire open reading frame for PTP-OB is inserted into the NdeI site of pET 11a. Constructs in the positive orientation are identified by sequence analysis and used to transform the expression host strain BL21. Transformants are then used to inoculate cultures for the production of PTP-OB protein. Cultures may be grown in M9 or ZB media, whose formulation is known to those skilled in the art. After growth to an approximate $OD_{600}$= 1.5, expression of PTP-OB is induced with 1 mM IPTG for 3 hours at 37° C. Authentic PTP-OB may be found in the insoluble inclusion body fraction from these cells. Soluble PTP-OB is extracted from the inclusion body fraction with 5M guanidine-HCl in a buffer containing 50 mM Tris-HCl (pH 8) and 100 mM dithiothreitol. Active PTP-OB is generated from this extract following dialysis against 100 volumes of 25 mM HEPES (pH 7.5), 5 mM dithiothreitol, 10% sucrose.

PTP assays. The cDNA coding for the cytoplasmic region (amino acid residues 69–699) of PTPε and PTP-OB were individually inserted in frame into the bacterial expression vector pGEX-2TX (Pharmacia), thus forming a glutathione S-transferase (GST) PTPε fusion protein and a GST-PTP-OB fusion protein. The GST-PTP-OB and GST-PTPε fusion proteins were isolated from the bacteria according to the Pharmacia protocol. The enzymatic assays were performed at optimal reaction conditions (50 mM MES, 0.15M NaCl, 10% glycerol, pH of 5.65) at ambient temperature. As a substrate fluorescine diphosphate (FDP, Molecular Probes, Inc., Eugene, Oreg.) at the Km was used. The reaction was continuously monitored by measuring the dephosphorylated product using a Millipore Cytoflour II plate reader with an excitation wavelength of 485 nm (20 nm band width) and an emission wavelength of 530 nm (30 nm band width). The recombinant PTP-OB enzyme, purified according to the directions provided by the plasmid pGEX-2TX manufacturer, was used in the assays described herein, such as in Examples 10 and 11.

EXAMPLE 4
In Vitro Translation of PTP-OB mRNA and Xenopus Oocyte Expression

PTP-OB cDNA constructs are ligated into in vitro transcription vectors (the pGEM series, Promega) for the production of synthetic mRNAs.

Synthetic mRNA is produced in sufficient quantity in vitro by cloning double stranded DNA encoding PTP-OB mRNA into a plasmid vector containing a bacteriophage promoter, linearizing the plasmid vector containing the cloned PTP-OB-encoding DNA, and transcribing the cloned DNA in vitro using a DNA-dependent RNA polymerase from a bacteriophage that specifically recognizes the bacteriophage promoter on the plasmid vector.

Various plasmid vectors are available containing a bacteriophage promoter recognized by a bacteriophage DNA-dependent RNA polymerase, including but not limited to plasmids pSP64, pSP65, pSP70, pSP71, pSP72, pSP73, pGEM-3Z, pGEM-4Z, pGEM-3Zf, pGEM-5Zf, pGEM-7Zf, pGEM-9Zf, and pGEM-11Zf, the entire series of plasmids is commercially available from Promega.

The double stranded PTP-OB-encoding DNA is cloned into the bacteriophage promoter containing vector in the proper orientation using one or more of the available restriction endonuclease cloning sites on the vector which are convenient and appropriate for cloning PTP-OB DNA. The vector with the ligated PTP-OB DNA is used to transform bacteria, and clonal isolates are analyzed for the presence of the vector with the PTP-OB DNA in the proper orientation.

Once a vector containing the PTP-OB-encoding DNA in the proper orientation is identified and isolated, it is linearized by cleavage with a restriction endonuclease at a site downstream from, and without disrupting, the PTP-OB transcription unit. The linearized plasmid is isolated and purified, and used as a template for in vitro transcription of PTP-OB mRNA.

The template DNA is then mixed with bacteriophage-specific DNA-dependent RNA polymerase in a reaction mixture which allows transcription of the DNA template forming PTP-OB mRNA. Several bacteriophage-specific DNA-dependent RNA polymerases are available, including but not limited to T3, T7, and SP6 RNA polymerase. The synthetic PTP-OB mRNA is then isolated and purified.

It may be advantageous to synthesize mRNA containing a 5' terminal cap structure and a 3' poly A tail to improve mRNA stability. A cap structure, or 7-methylguanosine, may be incorporated at the 5'terminus of the mRNA by simply adding 7-methylguanosine to the reaction mixture with the DNA template. The DNA-dependent RNA polymerase incorporates the cap structure at the 5' terminus as it synthesizes the mRNA. The poly A tail is found naturally occurring in many cDNAs but can be added to the 3' terminus of the mRNA by simply inserting a poly A tail-encoding DNA sequence at the 3' end of the DNA template.

The isolated and purified PTP-OB mRNA is translated using either a cell-free system, including but not limited to rabbit reticulocyte lysate and wheat germ extracts (both commercially available from Promega and New England Nuclear) or in a cell based system, including but not limited to microinjection into Xenopus oocytes, with microinjection into Xenopus oocytes being preferred.

Xenopus oocytes are microinjected with a sufficient amount of synthetic PTP-OB mRNA to produce PTP-OB protein. The microinjected oocytes are incubated to allow translation of the PTP-OB mRNA, forming PTP-OB protein.

These synthetic mRNAs are injected into Xenopus oocytes (stage 5–6) by standard procedures [Gurdon, J. B. and Wickens, M. D. Methods in Enzymol. 101: 370–386, (1983)]. Oocytes are harvested and analyzed for PTP-OB expression.

EXAMPLE 6
Cloning of PTP-OB cDNA into a Mammalian Expression Vector

PTP-OB cDNA expression cassettes are ligated at appropriate restriction endonuclease sites to the following vectors containing strong, universal mammalian promoters: pBC12BI [Cullen, B. R. Methods in Enzymol. 152: 684–704 1988], and pEE12 (CellTech EP O 338,841) and its derivatives pSZ9016-1 and p9019. p9019 represents the construction of a mammalian expression vector containing the hCMVIE promoter, polylinker and SV40 polyA element with a selectable marker/amplification system comprised of a mutant gene for dihydrofolate reductase (mDHFR) (Simonsen, C. C. and Levinson, A. D. Proc. Natl. Acad. Sci USA 80: 2495–2499 [1983]) driven by the SV40 early promoter. An SV40 polyadenylation sequence is generated by a PCR reaction defined by primers 13978-120 and 139778-121 using pD5 (Berker and Sharp, Nucl. Acid Res. 13: 841–857 [1985]) as template. The resulting 0.25 Kb PCR product is digested with ClaI and SpeI and ligated into the 6.7 Kb fragment of pEE12 which had been likewise digested. The resultant plasmid is digested with BglII and SfiI to liberate the 3' portion of the SV40 early promoter and the GScDNA from the vector. A 0.73 Kb SfiI-XhoII fragment isolated from plasmid pFR400 (Simonsen, C. C. and Levinson, A. D. Proc. Natl. Acad. Sci USA 80: 2495–2499 [1983]) is ligated to the 5.6 Kb vector described above, reconstituting the SV40 early promoter, and inserting the mdHFR gene. This plasmid is designated p9019. pSZ9016-1 is identical to p9019 except for the substitution of the HIV LTR for the huCMVIE promoter. This vector is constructed by digesting p9019 with XbaI and MluI to remove the huCMVIE promoter. The HIV LTR promoter, from residue −117 to +80 (as found in the vector pCD23 containing the portion of the HIV-1 LTR (Cullen, Cell 46:973 [1986]) is PCR amplified from the plasmid pCD23 using oligonucleotide primers which appended to the ends of the product the MluI and SpeI restriction sites on the 5' side while Hind III and Xba I sites are appended on the 3' side. Following the digestion of the resulting 0.2 kb PCR product with the enzymes MluI and Xba I the fragment is agarose gel-purified and ligated into the 4.3 Kb promoterless DNA fragment to generate the vector pSZ9016-1.

Cassettes containing the PTP-OB cDNA in the positive orientation with respect to the promoter are ligated into appropriate restriction sites 3' of the promoter and identified by restriction site mapping and/or sequencing. These cDNA expression vectors are introduced into various host cells including, but not limited to: [COS-7 (ATCC# CRL1651), CV-1 tat [Sackevitz et al., Science 238: 1575 (1987)], 293, L (ATCC# CRL6362)] by standard methods including but not limited to electroporation, or chemical procedures (cationic liposomes, DEAE dextran, calcium phosphate). Transfected cells and cell culture extracts can be harvested and analyzed for PTP-OB expression as described below.

All of the vectors used for mammalian transient expression can be used to establish stable cell lines expressing PTP-OB. Unaltered PTP-OB cDNA constructs cloned into expression vectors will be expected to program host cells to make intracellular PTP-OB protein. The transfection host cells include, but are not limited to, CV-1-P [Sackevitz et al., Science 238: 1575 (1987)], tk-L [Wigler, et al. Cell 11: 223 (1977)], NS/0, and dHFr-CHO [Kaufman and Sharp, J. Mol. Biol. 159: 601, (1982)].

Co-transfection of any vector containing PTP-OB cDNA with a drug selection plasmid including, but not limited to G418, aminoglycoside phosphotransferase, pLNCX [Miller, A. D. and Rosman G. J. Biotech News 7: 980–990 (1989)]; hygromycin, hygromycin-B phosphotransferase, pLG90 [Gritz. L. and Davies, J., GENE 25: 179 (1983)]; APRT, xanthine-guanine phosphoribosyl-transferase, pMAM (Clontech) [Murray, et al., Gene 31: 233 (1984)] will allow for the selection of stably transfected clones. Levels of PTP-OB are quantitated by the assays described above.

PTP-OB cDNA constructs are ligated into vectors containing amplifiable drug-resistance markers for the production of mammalian cell clones synthesizing the highest possible levels of PTP-OB. Following introduction of these constructs into cells, clones containing the plasmid are selected with the appropriate agent, and isolation of an over-expressing clone with a high copy number of the plasmid is accomplished by selection in increasing doses of the agent. The following systems are utilized: the 9016 or the 9019 plasmid containing the mutant DHFR gene [Simonson, C. and Levinson, A., Proc. Natl. Acad. Sci. USA 80: 2495 (1983)], transfected into DHFR- CHO cells and selected in methotrexate; the pEE12 plasmid containing the glutamine synthetase gene, transfected into NS/O cells and selected in methionine sulfoximine (CellTech International Patent Application 2089/10404); and 9016 or other CMV promoter vectors, co-transfected with pDLAT-3 containing the thymidine kinase gene [Colbere and Garopin, F., Proc. Natl. Acad. Sci. 76: 3755 (1979)] in APRT and TK deficient L cells, selected in APRT (0.05 mM azaserine, 0.1 mM adenine, 4 ug/ml adenosine) and amplified with HAT (100 uM hypoxanthine, 0.4 uM aminopterin, 16 uM thymidine).

EXAMPLE 7
Cloning of PTP-OB cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing PTP-OB cDNA is produced by the following standard methods (InVitrogen Maxbac Manual): the PTP-OB cDNA constructs are ligated downstream of the polyhedrin promoter in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells (Summers, M. D. and Smith, G. E., Texas Agriculture Exp. Station Bulletin No. 1555) and recombinant pBlueBac viruses are identified on the basis of β-galactosidase expression (Vialard, et al. 1990, J. Virol., 64, pp 37–50). Following plaque purification and infection of sf9 cells with PTP-OB recombinant baculovirus, PTP-OB expression is measured by the assays described above.

The cDNA encoding the entire open reading frame for PTP-OB is inserted into the BamHI site of pBlueBacII. Constructs in the positive orientation with respect to the polyhedrin promoter are identified by sequence analysis and used to transfect Sf9 cells in the presence of linear AcNPV mild type DNA.

EXAMPLE 8
Cloning of PTP-OB cDNA into a Yeast Expression Vector

Recombinant PTP-OB is produced in the yeast S. cerevisiae following the insertion of the optimal PTP-OB cDNA construct into expression vectors designed to direct the intracellular expression of heterologous proteins. For intracellular expression, vectors such as EmBLyex4 or the like are ligated to the PTP-OB cistron [Rinas, U. et al., Biotechnology 8: 543–545 (1990); Horowitz B. et al., J. Biol. Chem. 265: 4189–4192 (1989)]. The levels of expressed PTP-OB are determined by the assays described above.

EXAMPLE 9
Purification of Recombinant PTP-OB

Recombinantly produced PTP-OB may be purified by antibody affinity chromatography.

PTP-OB antibody affinity columns are made by adding the anti-PTP-OB antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing agents, if necessary such as detergents, and the cell culture supernatants or cell extracts containing PTP-OB or PTP-OB fragments are slowly passed through the column. The column is then washed with phosphate-buffered saline together with detergents, if necessary until the optical density (A280) falls to background, then the protein is eluted with 0.23M glycine-HCl (pH 2.6) together with detergents, if necessary. The purified PTP-OB protein is then dialyzed against phosphate buffered saline.

EXAMPLE 10
Screening Assay to Identify Modulators of PTP Activity

Mouse osteoclasts were generated in vitro by culturing together bone marrow cells and calvariae osteoblasts. Osteoblastic cells were isolated from mouse calvariae and cultured for 24 hours. Then, freshly isolated bone marrow cells were added to the cultured osteoblasts and treated with 10 nM 1,25(OH)2D3 (D3) for seven days. Under these conditions the bone marrow cells differentiated into multinucleated osteoclast-like cells that were positively stained for tartarat resistant alkaline phosphatase (TRAP), have other osteoclast specific markers (Takahashi, N. T. et al., 1988, Endocrinol., 123, pp.2600–2602), and have the ability to resorb bone in culture. The D3 and the various inhibitors were added to the cells with fresh medium at days two and four of co-culturing. TRAP positive cells were counted in quadruplicate wells for each test condition.

Mouse bone marrow cells, were induced to differentiate into osteoclast-like cells by co-culturing with neonatal calvariae osteoblasts in a D3 dependent process. These cells were stained by tartarat resistant acid phosphatase and exhibited markers that were associated with osteoclasts, such as calcitonin receptors, and vitronectin receptors. Furthermore, like osteoclasts, the cells contained multiple nuclei as a result of cell fusion activities (Takahashi, N. T. et al., supra). The multinucleated TRAP positive cells could be recognized as early as four days of co-culturing, but the majority of the multinucleated osteoclast-like cells (70–80%) were generated after six and seven days of co-culturing. The process was completely dependent on the treatment with vitamin D3, and no osteoclasts were formed in the absence of either D3, osteoblasts or bone marrow cells (Takahashi, N. T. et al., supra ).

Figure 5A:
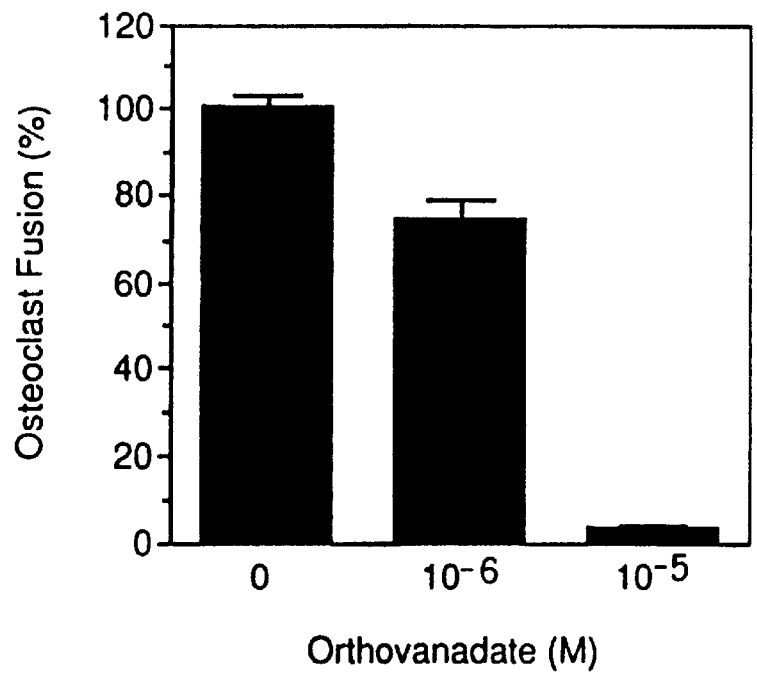
FIGS. 5A–C The effect of protein tyrosine phosphatases and protein tyrosine kinase in in vitro osteoclast formation is shown in the presence of (A) orthovanadate, (B) PAO, and (C) geldanamycin.
Figure 5B:
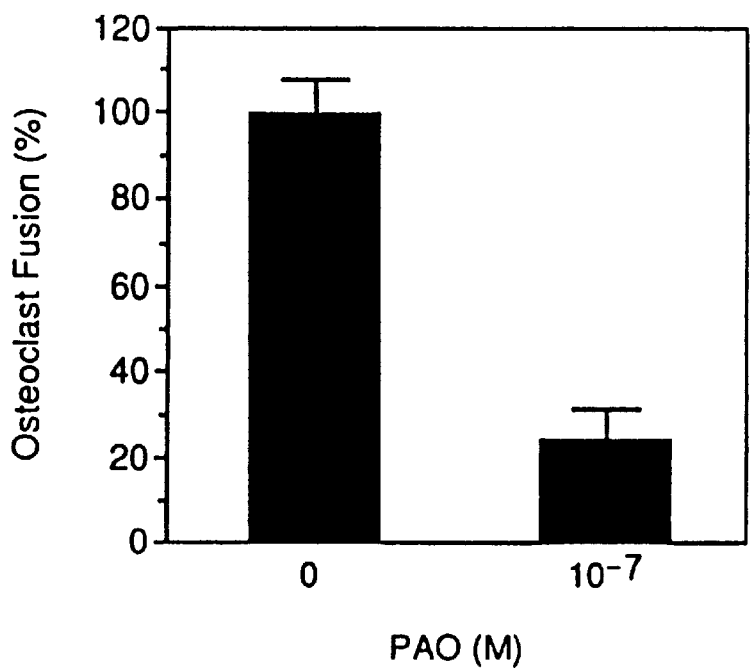

To test for the importance of PTPase activity in the generation of osteoclasts, we studied the influence of PTPase inhibitors on the differentiation of bone marrow cells in osteoclast. In these experiments, addition of orthovanadate to the co-cultured cells completely inhibited the formation of the multinucleated TRAP positive cells, with an IC 50 of 2 $\mu$M (FIG. 5A). Similarly, treatment with phenylarsine oxide (PAO) strongly inhibited the formation of the multinucleated TRAP positive cells with an IC 50 of 0.2 $\mu$M (FIG. 5B). Treatment with orthovanadate (10 $\mu$M) or phenylarsine oxide (0.2 $\mu$M), which markedly inhibited the formation of the fused TRAP positive cells, produced mononucleated TRAP positive cells. Thus, the major influence of the inhibitors appeared to be on the process of cell fusion. Moreover, at these concentration of PTPase inhibitors, no ill effects were observed on the co-cultured osteoblasts. To further characterize the importance of the PTPases on osteoclast formation, orthovanadate was added at different days of co-culturing and the formation of fused TRAP positive cells was measured.

Figure 5C:
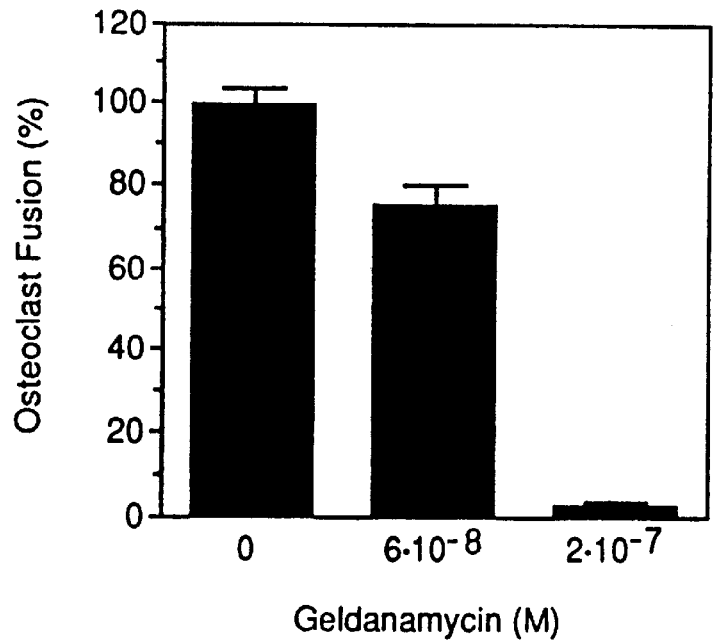
Figure 6:
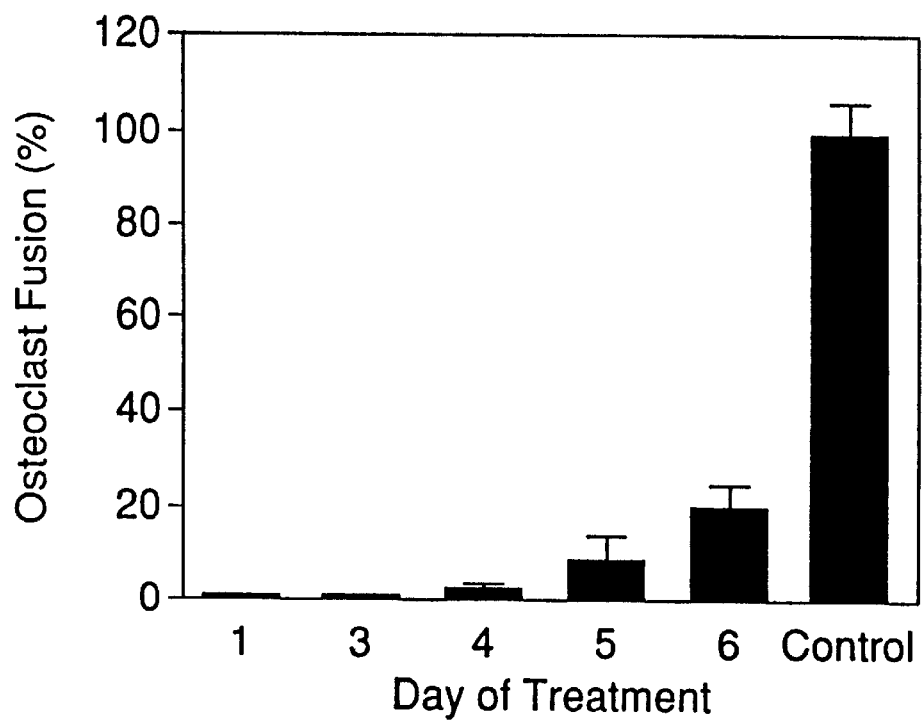
FIG. 6 The time dependent effect of orthovanadate on osteoclast cell fusion is shown.

In these experiments the orthovanadate was able to block 80% of the formation of the multinucleated TRAP positive cells when added at six days of co-culturing (FIG. 6). Addition of the PTPase inhibitor at earlier days of the co-culturing before the major cell fusion occurred had a small additional effect. To further study the role of tryosine phosphorylation in osteoclast formation, influence of geldanamycin, a tyrosine kinase inhibitor, on the formation of osteoclasts was tested. In these experiments, geldanamycin was a potent inhibitor of osteoclasts formation, with an IC 50 of 50 ng/ml (FIG. 5C). Though, in contrast to the PTPase inhibitors, it completely blocked the appearance of mononuclear TRAP positive cells.

Figure 7A:
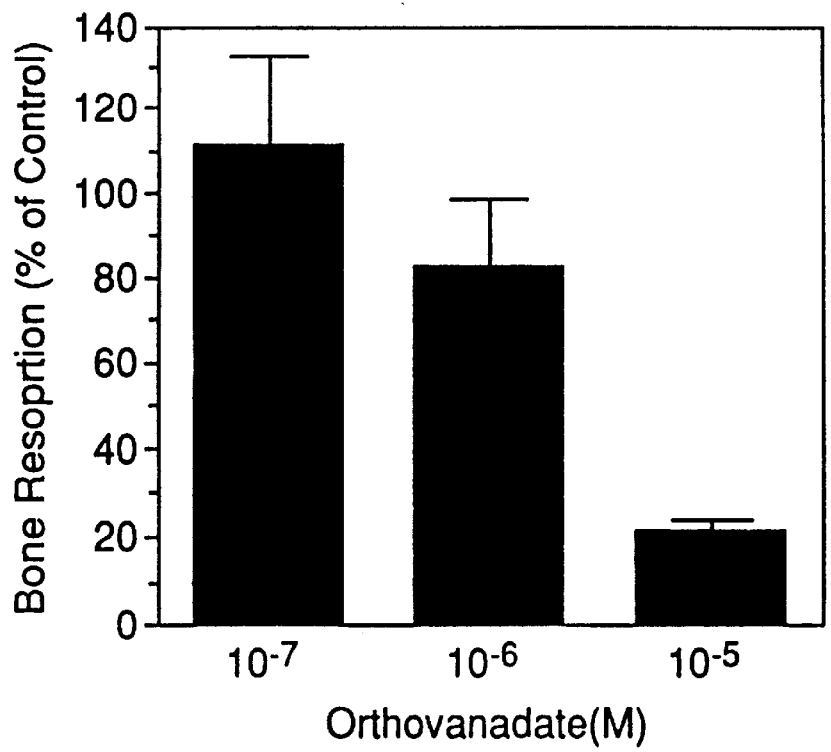
FIGS. 7A–B The effect of inhibitors of protein tyrosine phosphatases and protein tyrosine kinase on in vitro bone resorption is shown in the presence of (A) orthovanadate, and (B) PAO.
Figure 7B:
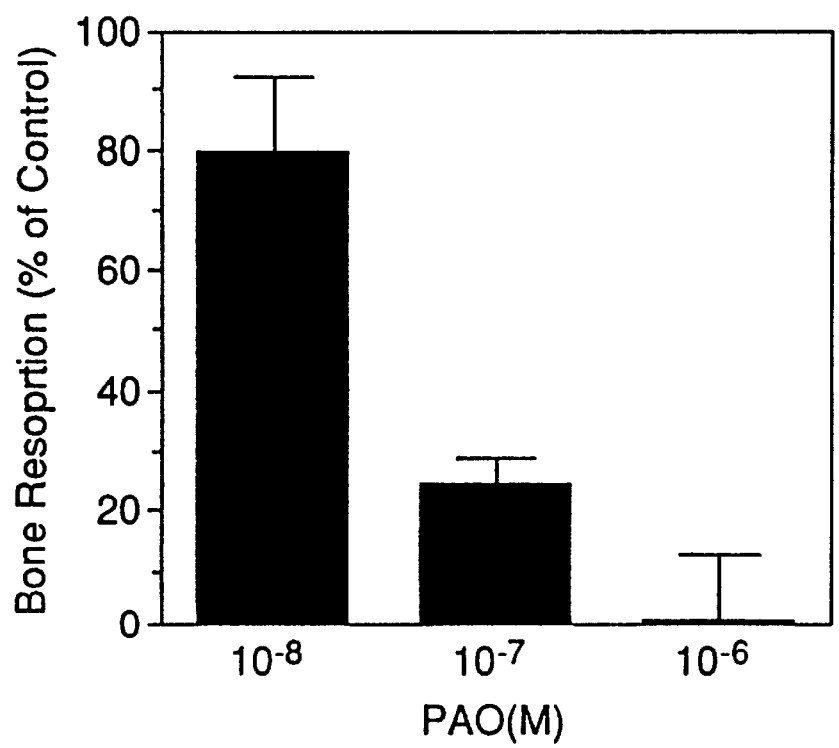

To test whether PTPase activity could influence the osteoclasts activity, the influence of the PTPase inhibitors was tested in an in vitro bone resorption assay. In these assays, freshly isolated rat osteoclasts were placed on bone slices for 24 hours and the influence of PTPase inhibitors on the number of resorbing pits in the bone slice were observed. Both orthovanadate and phenylarsine oxide were found to be potent inhibitors of bone resorption, with an IC50 of 2 $\mu$M for orthovanadate (FIG. 7A) and IC 50 of 0.05 $\mu$M for penylarsine oxide (FIG. 7B).

Bone Resorption Assay. Six long bones were isolated from neonatal rats and were placed in 4.5 ml 199 medium supplemented with 10% fetal bovine serum. The bones were dissected longitudinally and cells were separated by scraping. The cell suspension was filtered through a nylon mesh. Circular slices of steer bone (4.4×0.2 mm) were sonicated, sterilized and then hydrated in culture medium. The isolated cells (0.1 ml) were placed on the bone slices in 96 well tissue culture plates and incubated at 37° C., 5% $CO_2$ with a PTP inhibitor or vehicle for 24 hours. At the end of the experiment, the bone slices were sonicated, fixed with ethanol and stained with methylene blue. The resorption pits were visualized by reflection light microscopy and their number was determined [Murrills, R. J., L. S. Stein, C. P. Fey, and D. W. Dempster. 1990. The effects of parathyroid hormone (PTH) and PTH-related peptide on osteoclast resorption of bone slices in vitro: an analysis of pit size and the resorption focus. *Endocrinology* 127:2648–2653].

Figure 8A:
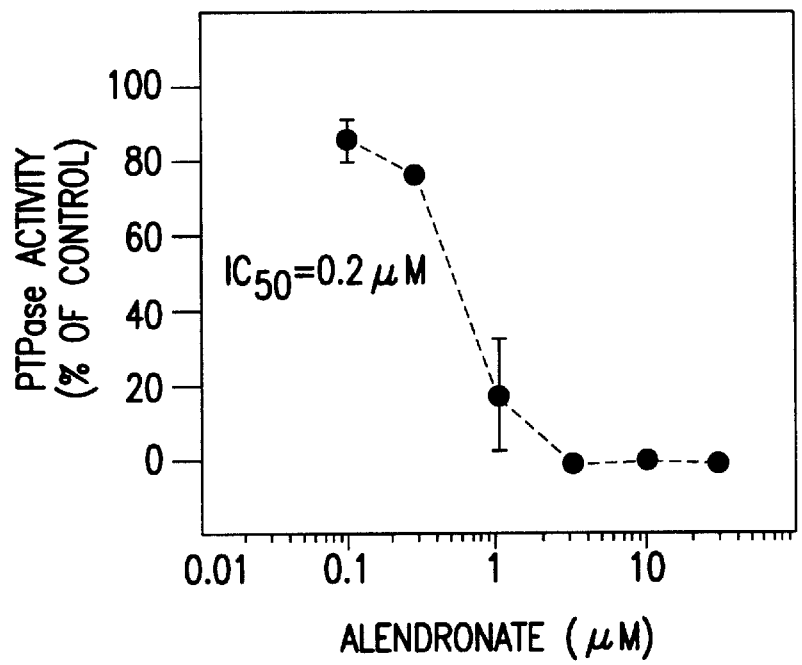
FIGS. 8A–B The enzymatic activity of recombinant PTP-OB is shown (A) alendronate, and (B) vanadate in the presence and absence of inhibitors.
Figure 8B:
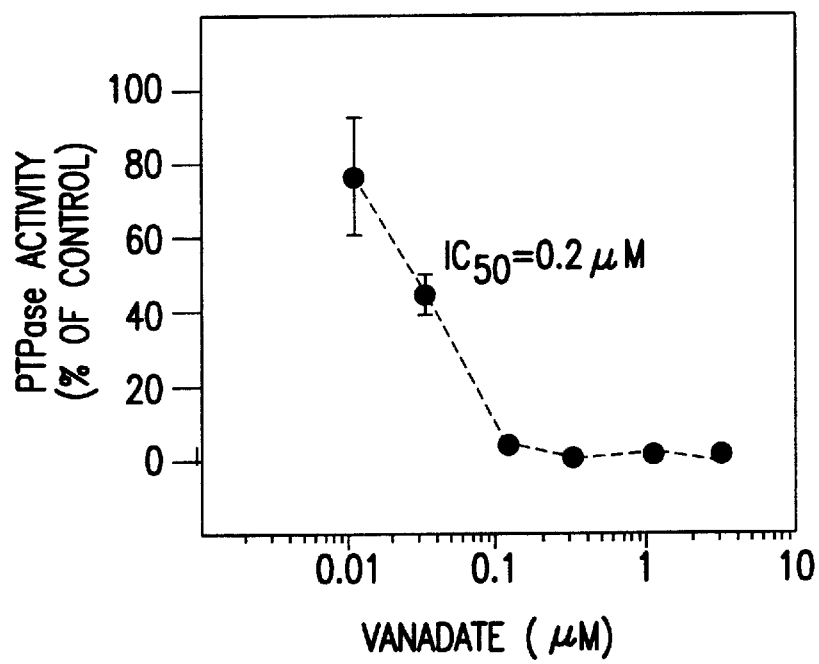

Alendronate inhibition of PTP activity. To study the enzymatic activity of PTP-OB and PTP$\epsilon$, we expressed the cytoplasmic domain of PTP-OB and PTP$\epsilon$ in bacteria as a GST-fusion protein. After purification, the GST-PTP-OB and GST-PTP$\epsilon$ fusion proteins were tested for PTP enzymatic activity and for their sensitivity to ALN and the PTP inhibitors, orthovanadate, BP, and PAO [Gordon, J. A. 1991. Use of vanadate as protein-phosphotyrosine phosphatase inhibitor. *Methods Enzymol.* 201:477–482; Walton, K. M., and J. E. Dixon. 1993. Protein tyrosine phosphatases. *Annu. Rev. Biochem.* 62:101–120] (FIG. 8). As a substrate we used FDP, previously described as a good substrate for other PTPases (34,35). PTP$\epsilon$ effectively dephosphorylated FDP with a Km=70 $\mu$M, which is comparable to the Km values obtained for other PTPs, such as CD45, PTP$\beta$ and PTP1B. As reported with other phosphatases, the enzymatic activity of PTP-OB was sensitive to orthovanadate ($IC_{50}$ of about 0.02 uM).

BPs are organic phosphate analogues that inhibit enzymatic activities of PTP that were expressed in osteoclasts. Therefore, we tested the influence of alendronate, a potent inhibitor of bone resorption, on the enzymatic activity of PTP-OB. In these studies, we determined that alendronate is also a potent inhibitor of PTP-OB with an $IC_{50}$ of 0.2 $\mu$M. Etidronate, another bisphosphonate, also inhibited PTP$\epsilon$ activity with an $IC_{50}$ of about 0.4 uM. Similar results were obtained when the GST moiety of the GST-PTP-OB protein fusion was cleaved with thrombin producing PTP-OB without the GST portion covalently attached.

BPs stimulate osteoblast proliferation It was reported that orthovanadate can stimulate osteoblast proliferation. Therefore to determine whether this effect is mediated via the inhibition of PTPs, we tested whether alendronate etidronate and orthovanadate can similarly stimulate the proliferation of the mouse calvaria derived MB1.8 cells. Orthovanadate, alendronate and etidronate stimulated thymidine incorporation (mitogenesis) of quiescent osteoblasts at micromolar concentrations, demonstrating proliferation of the cells.

Figure 9A:
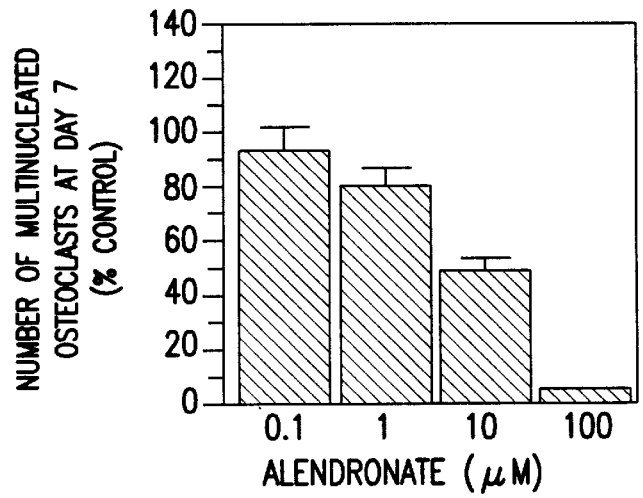
FIGS. 9A–C The inhibition of bone resorption is shown by inhibition of PTP-OB by (A) Alendronate, (B) vanadate and (C) PAO.
Figure 9B:
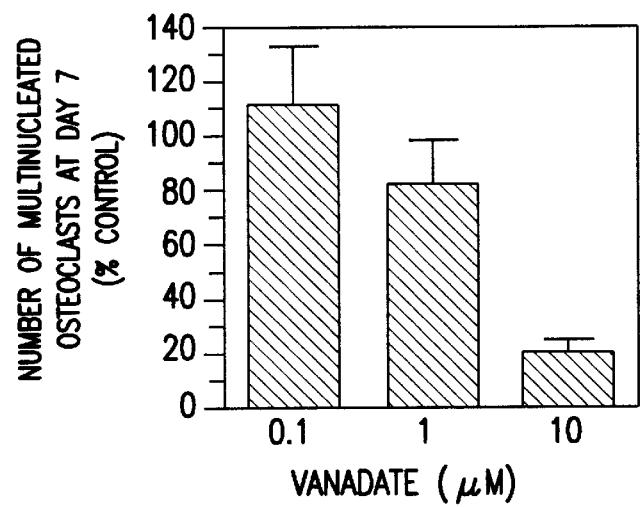
Figure 9C:
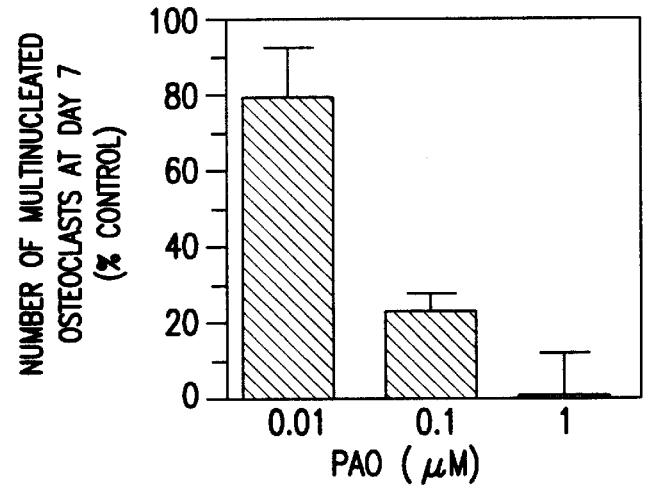

Requirement of PTP Activity for Bone Resorption. To determine a possible relationship between ALN inhibition of PTP activity and inhibition of bone resorption, we compared the effects of ALN (FIG. 9A), orthovanadate (FIG. 9B) and PAO (FIG. 9C) on in vitro bone resorption by rat osteoclasts. All three inhibitors (ALN, orthovanadate and PAO) inhibited the osteoclast-mediated bone resorption, reducing the number of resorption pits by 80% at $10^{-5}$M, $10^{-5}$M and $10^{-6}$M, respectively. These findings suggest that PTP activity in osteoclasts is essential for bone resorption.

Figure 10A:
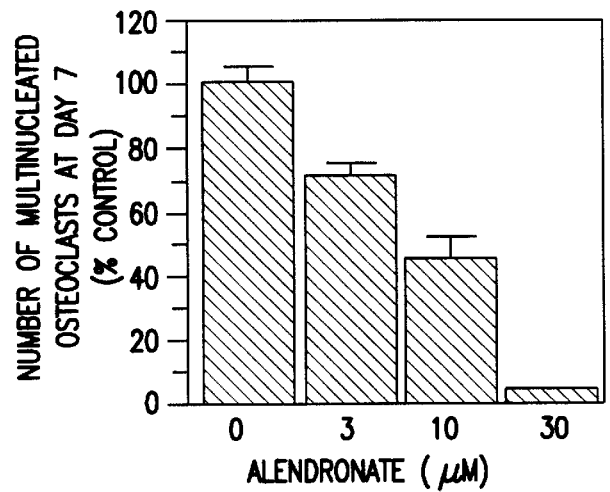
FIGS. 10A–D Inhibition of formation of multinucleated TRAP positive cells by PTP inhibitors (A) alendronate, (B) orthovanadate and (C) PAO; and, (D) time course (day 1–6) inhibition of formation of multinucleated TRAP positive cells by the PTP inhibitor orthovanadate.
Figure 10B:
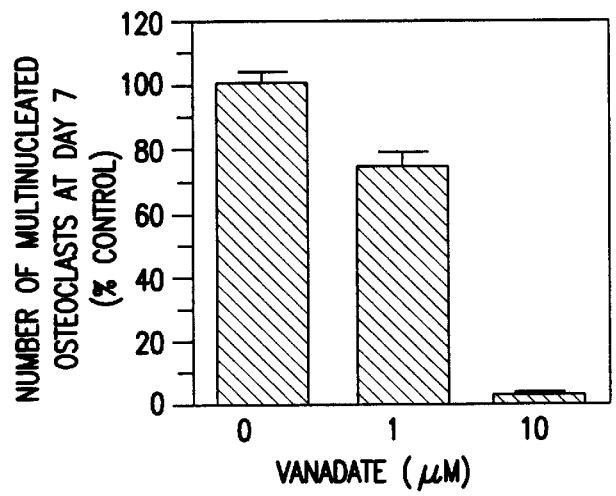
Figure 10C:
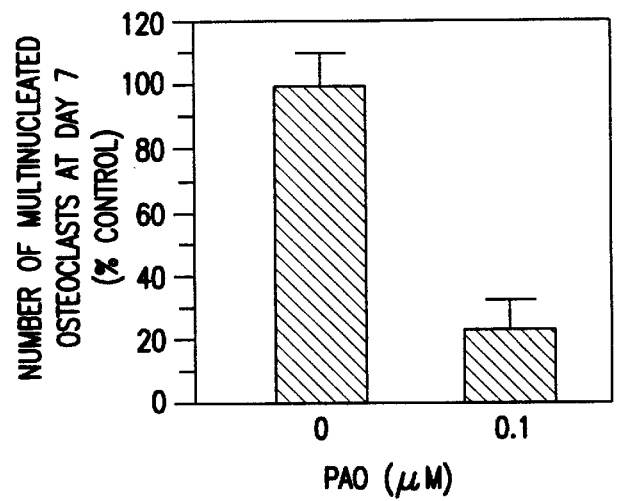

The Role of PTP Activity for Osteoclast Differentiation. It has been previously reported that bisphosphonates inhibit osteoclast formation in culture [Hughes, D. E., B. R. MacDonald, R. G. Russell, and M. Gowen. 1989. Inhibition of osteoclast-like cell formation by bisphosphonates in longterm cultures of human bone marrow. J. Clin. Invest. 83:1930–1935]. We compared the effects of the three PTP inhibitors in this in vitro osteoclast formation system. Co-cultured mouse bone marrow cells and mouse calvaria osteoblasts were treated after two days with one of the PTP inhibitors, and the number of multinucleated TRAP positive cells was determined at day seven of co-culture. ALN (FIG. 10A), orthovanadate (FIG. 10B) and PAO (FIG. 10C) completely inhibited the formation of multinucleated TRAP positive cells at $10^{-5}$M, $10^{-5}$M and $2\times10^{-7}$M, respectively, but did not block the development of mononucleated TRAP positive cells, suggesting that the three compounds inhibit osteoclast formation at a similar step in the maturation pathway. At the respective concentrations, the three PTP inhibitors, had no apparent toxicity for either osteoblasts or bone marrow cells.

Figure 10D:
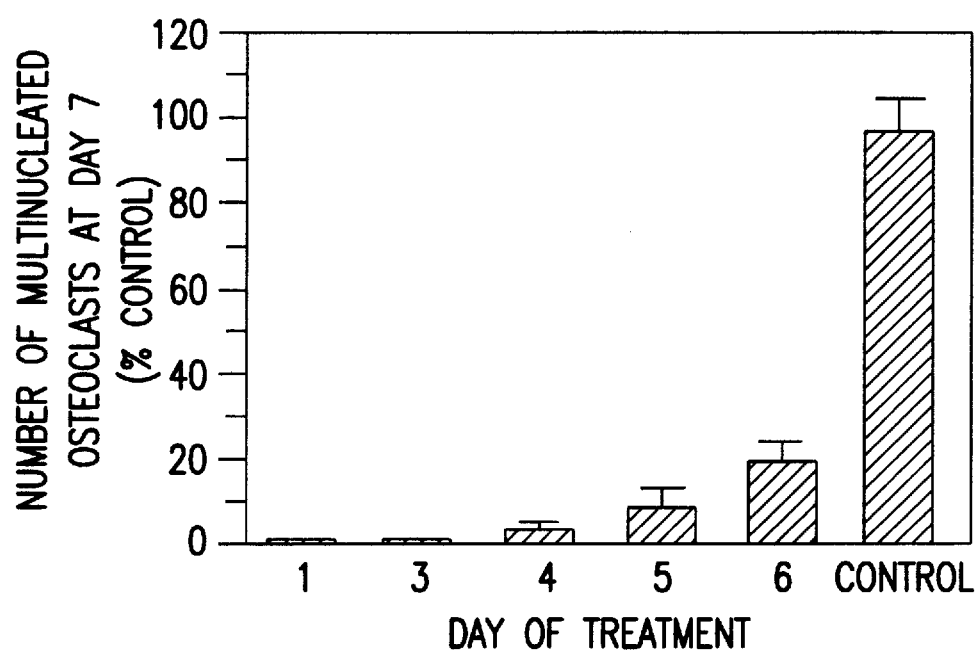

To further test the requirement for PTP activity during osteoclast formation, we added orthovanadate at different times of co-culture and counted the number of multinucleated TRAP positive cells at seven days. We found that addition of orthovanadate at any time up to day six of the co-culture inhibited the formation of multinucleated osteoclastic cells by 90% or more. Addition at day six (last 24 hours) caused 80% inhibition (FIG. 10D). These findings suggest that PTP activity is essential during a late stage in the formation of multinucleated TRAP positive cells.

Inhibition of osteoclast formation by tyrosine kinase inhibitors was recently reported [Hall, T. J., M. Schaeublin, and M. Missbach. 1994. Evidence that c-src is involved in the process of osteoclastic bone resorption. Biochem. Biophys. Res. Commun. 199:1237–1244; Yoneda, T., C. Lowe, C. H. Lee, G. Gutierrez, M. Niewolna, P. J. Williams, E. Izbicka, Y. Uehara, and G. R. Mundy. 1993. Herbimycin A, a pp60 c-src tyrosine kinase inhibitor, inhibits osteoclastic bone resorption in vitro and hypercalcemia in vivo. J. Clin. Invest. 91:2791–2795]. We found that the tyrosine kinase inhibitor, geldanamycin, also inhibited the differentiation of bone marrow cells into multinucleated TRAP positive cells, complete inhibition occurring at $2\times10^{-7}$M. However, in contrast to the effects of PTP inhibitors, geldanamycin treatment inhibited the development of mononuclear TRAP positive cells, suggesting effects at an earlier stage of osteoclast maturation.

EXAMPLE 11

Recombinant protein tyrosine phosphatase PTP-OB is expressed in a recombinant host cell (as in Examples 1–10) in native form or as a hybrid or fusion protein. PTP-OB is then used in an enzymatic assay for tyrosine phosphatase activity in a suitable buffer (0.1M TRIS-HCL, pH 7.4; 1 mM EDTA; 50 mM NaCl; 1 mM DTT). As a substrate, a phosphorylated peptide or protein is added as well as phosphorylated tyrosine or similar molecule. The release of phosphate is measured by colorimetric assay or by the release of radiolabelled phosphate. Various inhibitors are added to the assay reaction to determine their inhibitory effect on the enzymatic activity of PTP-OB. The potential inhibitor substances for use in this assay are produced synthetically or are isolated from natural sources.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

CTTCTAGAAR TGYGCNCART AYTGGCC        27

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Lys Cys Ala Gln Tyr Trp Pro
1                       5

( 2 ) INFORMATION FOR SEQ ID NO:3:

( i ) SEQUENCE CHARACTERISTICS:

-continued ( A ) LENGTH: 30 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

GAAGCTTCCM AYNCCTGCAC WRCARTGNAC                                       30

( 2 ) INFORMATION FOR SEQ ID NO:4:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

Val His Cys Ser Ala Gly Val Gly
1               5

( 2 ) INFORMATION FOR SEQ ID NO:5:

( i ) SEQUENCE CHARACTERISTICS:
( A ) LENGTH: 1911 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:5:

Met Ala Pro Thr Trp Gly Pro Gly Met Val Ser Val Val Gly Pro Met
1               5                   10                  15

Gly Leu Leu Val Val Leu Leu Val Gly Gly Cys Ala Ala Glu Glu Pro
            20                  25                  30

Pro Arg Phe Ile Lys Glu Pro Lys Asp Gln Ile Gly Val Ser Gly Arg
        35                  40                  45

Val Ala Ser Phe Val Cys Gln Ala Thr Gly Asp Pro Lys Pro Arg Val
    50                  55                  60

Thr Trp Asn Lys Lys Gly Lys Lys Val Asn Ser Gln Arg Phe Glu Thr
65                  70                  75                  80

Ile Glu Phe Asp Glu Ser Ala Gly Ala Val Leu Arg Ile Gln Pro Leu
                85                  90                  95

Arg Thr Pro Arg Asp Glu Asn Val Tyr Glu Cys Val Ala Gln Asn Ser
            100                 105                 110

Val Gly Glu Ile Thr Val His Ala Lys Leu Thr Val Leu Arg Glu Asp
        115                 120                 125

Gln Leu Pro Ser Gly Phe Pro Asn Ile Asp Met Gly Pro Gln Leu Lys
    130                 135                 140

Val Val Glu Arg Thr Arg Thr Ala Thr Met Leu Cys Ala Ala Ser Gly
145                 150                 155                 160

Asn Pro Asp Pro Glu Ile Thr Trp Phe Lys Asp Phe Leu Pro Val Asp
                165                 170                 175

Pro Ser Ala Ser Asn Gly Arg Ile Lys Gln Leu Arg Ser Gly Ala Leu
            180                 185                 190

Gln Ile Glu Ser Ser Glu Glu Thr Asp Gln Gly Lys Tyr Glu Cys Val
        195                 200                 205

Ala Thr Asn Ser Ala Gly Val Arg Tyr Ser Ser Pro Ala Asn Leu Tyr

|     |     |     |     |     |     |     |     |     |     |     |     |     |     |     |
| --- | --- | --- | --- | --- | --- | --- | --- | --- | --- | --- | --- | --- | --- | --- |
|     |     | 210 |     |     |     |     | 215 |     |     |     |     | 220 |     |     |
| Val 225 | Arg | Val | Arg | Arg | Val 230 | Ala | Pro | Arg | Phe | Ser 235 | Ile | Leu | Pro | Met 240 | Ser |
| His | Glu | Ile | Met | Pro 245 | Gly | Gly | Asn | Val | Asn 250 | Ile | Thr | Cys | Val | Ala 255 | Val |
| Gly | Ser | Pro | Met 260 | Pro | Tyr | Val | Lys | Trp 265 | Met | Gln | Gly | Ala | Glu 270 | Asp | Leu |
| Thr | Pro | Glu 275 | Asp | Asp | Met | Pro | Val 280 | Gly | Arg | Asn | Val | Leu 285 | Glu | Leu | Thr |
| Asp | Val 290 | Lys | Asp | Ser | Ala | Asn 295 | Tyr | His | Pro | Cys | Val 300 | Ala | Met | Ser | Ser |
| Leu 305 | Gly | Val | Ile | Glu | Ala 310 | Val | Ala | Gln | Ile | Thr 315 | Val | Lys | Ser | Leu | Pro 320 |
| Lys | Ala | Pro | Gly | Thr 325 | Pro | Met | Val | Thr | Glu 330 | Asn | Thr | Ala | Thr | Ser 335 | Ile |
| Thr | Ile | Thr | Trp 340 | Asp | Ser | Gly | Asn | Pro 345 | Asp | Pro | Val | Ser | Tyr 350 | Tyr | Val |
| Ile | Glu | Tyr 355 | Lys | Ser | Lys | Ser | Gln 360 | Asp | Gly | Pro | Tyr | Gln 365 | Ile | Lys | Glu |
| Asp | Ile 370 | Thr | Thr | Thr | Arg | Tyr 375 | Ser | Ile | Gly | Gly | Leu 380 | Ser | Pro | Asn | Ser |
| Glu 385 | Tyr | Glu | Ile | Trp | Val 390 | Ser | Ala | Val | Asn | Ser 395 | Ile | Gly | Gln | Gly | Pro 400 |
| Pro | Ser | Glu | Ser | Val 405 | Val | Thr | Arg | Thr | Glu 410 | Gln | Ala | Pro | Ala | Arg 415 |     |
| Pro | Pro | Arg | Asn 420 | Val | Gln | Ala | Arg | Met 425 | Leu | Ser | Ala | Thr | Thr 430 | Met | Ile |
| Val | Gln | Trp 435 | Glu | Glu | Pro | Val | Glu 440 | Pro | Asn | Gly | Leu | Ile 445 | Arg | Gly | Tyr |
| Arg | Val 450 | Tyr | Tyr | Thr | Met | Glu 455 | Pro | Glu | His | Pro | Val 460 | Gly | Asn | Trp | Gln |
| Lys 465 | His | Asn | Val | Asp | Asp 470 | Ser | Leu | Leu | Thr | Thr 475 | Val | Gly | Ser | Leu | Leu 480 |
| Glu | Asp | Glu | Thr | Tyr 485 | Thr | Val | Arg | Val | Leu 490 | Ala | Phe | Thr | Ser | Val 495 | Gly |
| Asp | Gly | Pro | Leu 500 | Ser | Asp | Pro | Ile | Gln 505 | Val | Lys | Thr | Gln | Gln 510 | Gly | Val |
| Pro | Gly | Gln | Pro 515 | Met | Asn | Leu | Arg | Ala 520 | Glu | Ala | Arg | Ser 525 | Glu | Thr | Ser |
| Ile | Thr | Leu 530 | Ser | Trp | Ser | Pro | Pro 535 | Arg | Gln | Glu | Ser | Ile 540 | Ile | Lys | Tyr |
| Glu 545 | Leu | Leu | Phe | Arg | Glu 550 | Gly | Asp | His | Gly | Arg 555 | Glu | Val | Gly | Arg | Thr 560 |
| Phe | Asp | Pro | Thr | Thr 565 | Ser | Tyr | Val | Val | Glu 570 | Asp | Leu | Lys | Pro | Asn 575 | Thr |
| Glu | Tyr | Ala | Phe 580 | Arg | Leu | Ala | Ala | Arg 585 | Ser | Pro | Gln | Gly | Leu 590 | Gly | Ala |
| Phe | Thr | Pro 595 | Val | Val | Arg | Gln | Arg 600 | Thr | Leu | Gln | Ser | Lys 605 | Pro | Ser | Ala |
| Pro | Pro | Gln 610 | Asp | Val | Lys | Cys 615 | Val | Ser | Val | Arg | Ser 620 | Thr | Ala | Ile | Leu |
| Val 625 | Ser | Trp | Arg | Pro | Pro 630 | Pro | Pro | Glu | Thr | His 635 | Asn | Gly | Ala | Leu | Val 640 |

```
Gly Tyr Ser Val Arg Tyr Arg Pro Leu Gly Ser Glu Asp Pro Glu Pro
                645                 650                 655
Lys Glu Val Asn Gly Ile Pro Pro Thr Thr Gln Ile Leu Leu Glu
            660                 665                 670
Ala Leu Glu Lys Trp Thr Gln Tyr Arg Ile Thr Thr Ala His Thr
        675                 680                 685
Glu Val Gly Pro Gly Pro Glu Ser Ser Pro Val Val Arg Thr Asp
    690                 695                 700
Glu Asp Val Pro Ser Ala Pro Pro Arg Lys Val Glu Ala Glu Ala Leu
705                 710                 715                 720
Asn Ala Thr Ala Ile Arg Val Leu Trp Arg Ser Pro Ala Pro Gly Arg
                725                 730                 735
Gln His Gly Gln Ile Arg Gly Tyr Gln Val His Tyr Val Arg Met Glu
                740                 745                 750
Gly Ala Glu Ala Arg Gly Pro Pro Arg Ile Lys Asp Val Met Leu Ala
            755                 760                 765
Asp Ala Gln Glu Met Val Ile Thr Asn Leu Gln Pro Glu Thr Ala Tyr
        770                 775                 780
Ser Ile Thr Val Ala Ala Tyr Thr Met Lys Gly Asp Gly Ala Arg Ser
785                 790                 795                 800
Lys Pro Lys Val Val Val Thr Lys Gly Ala Val Leu Gly Arg Pro Thr
                805                 810                 815
Leu Ser Val Gln Gln Thr Pro Glu Gly Ser Leu Leu Ala Arg Trp Glu
                820                 825                 830
Pro Pro Ala Gly Thr Ala Glu Asp Gln Val Leu Gly Tyr Arg Leu Gln
            835                 840                 845
Phe Gly Arg Glu Asp Ser Thr Pro Leu Ala Thr Leu Glu Phe Pro Pro
        850                 855                 860
Ser Glu Asp Arg Tyr Thr Ala Ser Gly Val His Lys Gly Ala Thr Tyr
865                 870                 875                 880
Val Phe Arg Leu Ala Ala Arg Ser Pro Gly Gly Leu Gly Glu Glu Ala
                885                 890                 895
Ala Glu Val Leu Ser Ile Pro Glu Asp Thr Pro Arg Gly His Pro Gln
            900                 905                 910
Ile Leu Glu Ala Ala Gly Asn Ala Ser Ala Gly Thr Val Leu Leu Arg
        915                 920                 925
Trp Leu Pro Pro Val Pro Ala Glu Arg Asn Gly Ala Ile Val Lys Tyr
    930                 935                 940
Thr Val Ala Val Arg Glu Ala Gly Ala Leu Gly Pro Ala Arg Glu Thr
945                 950                 955                 960
Glu Leu Pro Ala Gly Arg Leu Ser Arg Ala Arg Arg Thr Leu Thr Leu
                965                 970                 975
Gln Gly Leu Lys Pro Asp Thr Ala Tyr Asp Leu Gln Val Arg Ala His
            980                 985                 990
Thr Arg Arg Gly Pro Gly Pro Phe Ser Pro Val Arg Tyr Arg Thr
        995                 1000                1005
Phe Leu Arg Asp Gln Val Ser Pro Lys Asn Phe Lys Val Lys Met Ile
        1010                1015                1020
Met Lys Thr Ser Val Leu Leu Ser Trp Glu Phe Pro Asp Asn Tyr Asn
1025                1030                1035                1040
Ser Pro Thr Pro Tyr Lys Ile Gln Tyr Asn Gly Leu Thr Leu Asp Val
                1045                1050                1055
Asp Gly Arg Thr Thr Lys Lys Leu Ile Thr His Leu Lys Pro His Thr
                1060                1065                1070
```

```
Phe Tyr Asn Phe Val Leu Thr Asn Arg Gly Ser Ser Leu Gly Gly Leu
            1075                1080                1085
Gln Gln Thr Val Thr Ala Trp Thr Ala Phe Asn Leu Leu Asn Gly Lys
            1090                1095                1100
Pro Ser Val Ala Pro Lys Pro Asp Ala Asp Gly Phe Ile Met Val Tyr
1105                1110                1115                1120
Leu Pro Asp Gly Gln Ser Pro Val Pro Val Gln Ser Tyr Phe Ile Val
            1125                1130                1135
Met Val Pro Leu Arg Lys Ser Arg Gly Gln Phe Leu Thr Pro Leu
            1140                1145                1150
Gly Ser Pro Glu Asp Met Asp Leu Glu Glu Leu Ile Gln Asp Ile Ser
            1155                1160                1165
Arg Leu Gln Arg Arg Ser Leu Arg His Ser Arg Gln Leu Glu Val Pro
            1170                1175                1180
Arg Pro Tyr Ile Ala Ala Arg Phe Ser Val Leu Pro Pro Thr Phe His
1185                1190                1195                1200
Pro Gly Asp Gln Lys Gln Tyr Gly Gly Phe Asp Asn Arg Gly Leu Glu
            1205                1210                1215
Pro Gly His Arg Tyr Val Leu Phe Val Leu Ala Val Leu Gln Lys Ser
            1220                1225                1230
Glu Pro Thr Phe Ala Ala Ser Pro Phe Ser Asp Pro Phe Gln Leu Asp
            1235                1240                1245
Asn Pro Asp Pro Gln Pro Ile Val Asp Gly Glu Glu Gly Leu Ile Trp
            1250                1255                1260
Val Ile Gly Pro Val Leu Ala Val Val Phe Ile Ile Cys Ile Val Ile
1265                1270                1275                1280
Ala Ile Leu Leu Tyr Lys Asn Lys Pro Asp Ser Lys Arg Lys Asp Ser
            1285                1290                1295
Glu Pro Arg Thr Lys Cys Leu Leu Asn Asn Ala Asp Leu Ala Pro His
            1300                1305                1310
His Pro Lys Asp Pro Val Glu Met Arg Arg Ile Asn Phe Gln Thr Pro
            1315                1320                1325
Gly Met Leu Ser His Pro Pro Ile Pro Ile Ala Asp Met Ala Glu His
            1330                1335                1340
Thr Glu Arg Leu Lys Ala Asn Asp Ser Leu Lys Leu Ser Gln Glu Tyr
1345                1350                1355                1360
Glu Ser Ile Asp Pro Gly Gln Gln Phe Thr Trp Glu His Ser Asn Leu
            1365                1370                1375
Glu Val Asn Lys Pro Lys Asn Arg Tyr Ala Asn Val Ile Ala Tyr Asp
            1380                1385                1390
His Ser Arg Val Ile Leu Gln Pro Ile Glu Gly Ile Met Gly Ser Asp
            1395                1400                1405
Tyr Ile Asn Ala Asn Tyr Val Asp Gly Tyr Arg Arg Gln Asn Ala Tyr
            1410                1415                1420
Ile Ala Thr Gln Gly Pro Leu Pro Glu Thr Phe Gly Asp Phe Trp Arg
1425                1430                1435                1440
Met Val Trp Glu Gln Arg Ser Ala Thr Ile Val Met Met Thr Arg Leu
            1445                1450                1455
Glu Glu Lys Ser Arg Ile Lys Cys Asp Gln Tyr Trp Pro Asn Arg Gly
            1460                1465                1470
Thr Glu Thr Tyr Gly Phe Ile Gln Val Thr Leu Leu Asp Thr Ile Glu
            1475                1480                1485
Leu Ala Thr Phe Cys Val Arg Thr Phe Ser Leu His Lys Asn Gly Ser
```

-continued

```
                1490                      1495                      1500

Ser  Glu  Lys  Arg  Glu  Val  Arg  Gln  Phe  Gln  Phe  Thr  Ala  Trp  Pro  Asp
1505                      1510                     1515                     1520

His  Gly  Val  Pro  Glu  Tyr  Pro  Thr  Pro  Phe  Leu  Ala  Phe  Leu  Arg  Arg
                         1525                    1530                    1535

Val  Lys  Thr  Cys  Asn  Pro  Pro  Asp  Ala  Gly  Pro  Ile  Val  Val  His  Cys
                         1540                    1545                    1550

Ser  Ala  Gly  Val  Gly  Arg  Thr  Gly  Cys  Phe  Ile  Val  Ile  Asp  Ala  Met
               1555                    1560                    1565

Leu  Glu  Arg  Ile  Lys  Pro  Glu  Lys  Thr  Val  Asp  Val  Tyr  Gly  His  Val
               1570                    1575                    1580

Thr  Leu  Met  Arg  Ser  Gln  Arg  Asn  Tyr  Met  Val  Gln  Thr  Glu  Asp  Gln
1585                     1590                    1595                     1600

Tyr  Ser  Phe  Ile  His  Glu  Ala  Leu  Leu  Glu  Ala  Val  Gly  Cys  Gly  Asn
                    1605                    1610                    1615

Thr  Glu  Val  Pro  Ala  Arg  Ser  Leu  Tyr  Ala  Tyr  Ile  Gln  Lys  Leu  Ala
               1620                    1625                    1630

Gln  Val  Glu  Pro  Gly  Glu  His  Val  Thr  Gly  Met  Glu  Leu  Glu  Phe  Lys
               1635                    1640                    1645

Arg  Leu  Ala  Asn  Ser  Lys  Ala  His  Thr  Ser  Arg  Phe  Ile  Ser  Ala  Asn
               1650                    1655                    1660

Leu  Pro  Cys  Lys  Lys  Phe  Lys  Asn  Arg  Leu  Val  Asn  Ile  Met  Pro  Tyr
1665                     1670                    1675                     1680

Glu  Ser  Thr  Arg  Val  Cys  Leu  Gln  Pro  Ile  Arg  Gly  Val  Glu  Gly  Ser
                    1685                    1690                    1695

Asp  Tyr  Ile  Asn  Ala  Ser  Phe  Ile  Asp  Gly  Tyr  Arg  Gln  Gln  Lys  Ala
                    1700                    1705                    1710

Tyr  Ile  Ala  Thr  Gln  Gly  Pro  Leu  Ala  Glu  Thr  Thr  Glu  Asp  Phe  Trp
               1715                    1720                    1725

Arg  Met  Leu  Trp  Glu  Asn  Asn  Ser  Thr  Ile  Val  Val  Met  Leu  Thr  Lys
               1730                    1735                    1740

Leu  Arg  Glu  Met  Gly  Arg  Glu  Lys  Cys  His  Gln  Tyr  Trp  Pro  Ala  Glu
1745                     1750                    1755                     1760

Arg  Ser  Ala  Arg  Tyr  Gln  Tyr  Phe  Val  Val  Asp  Pro  Met  Ala  Glu  Tyr
                         1765                    1770                    1775

Asn  Met  Pro  Gln  Tyr  Ile  Leu  Arg  Glu  Phe  Lys  Val  Thr  Asp  Ala  Arg
                    1780                    1785                    1790

Asp  Gly  Gln  Ser  Arg  Thr  Val  Arg  Gln  Phe  Gln  Phe  Thr  Asp  Trp  Pro
               1795                    1800                    1805

Glu  Gln  Gly  Val  Pro  Lys  Ser  Gly  Glu  Gly  Phe  Ile  Asp  Phe  Ile  Gly
               1810                    1815                    1820

Gln  Val  His  Lys  Thr  Lys  Glu  Gln  Phe  Gly  Gln  Asp  Gly  Pro  Ile  Ser
1825                     1830                    1835                     1840

Val  His  Cys  Ser  Ala  Gly  Val  Gly  Arg  Thr  Gly  Val  Phe  Ile  Thr  Leu
                         1845                    1850                    1855

Ser  Ile  Val  Leu  Glu  Arg  Met  Arg  Tyr  Glu  Gly  Val  Val  Asp  Ile  Phe
                    1860                    1865                    1870

Gln  Thr  Val  Lys  Met  Leu  Arg  Thr  Gln  Arg  Pro  Ala  Met  Val  Gln  Thr
               1875                    1880                    1885

Glu  Asp  Glu  Tyr  Gln  Phe  Cys  Tyr  Gln  Ala  Ala  Leu  Glu  Tyr  Leu  Gly
               1890                    1895                    1900

Ser  Phe  Asp  His  Tyr  Ala  Thr
1905                     1910
```

( 2 ) INFORMATION FOR SEQ ID NO:6:

( i ) SEQUENCE CHARACTERISTICS:
        ( A ) LENGTH: 6000 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

| | | | | | |
|---|---|---|---|---|---|
| GAATTCCGGG | TCGCTGCCAA | GCATGGCGCC | CACCTGGGGC | CCTGGCATGG | TGTCTGTGGT | 60 |
| TGGTCCCATG | GGCCTCCTTG | TGGTCCTGCT | CGTTGGAGGC | TGTGCAGCAG | AAGAGCCCCC | 120 |
| CAGGTTTATC | AAAGAACCCA | AGGACCAGAT | CGGCGTGTCG | GGGCGTGTGG | CCTCTTTCGT | 180 |
| GTGTCAGGCC | ACGGGTGACC | CCAAGCCACG | AGTGACCTGG | AACAAGAAGG | CAAGAAGGT | 240 |
| CAACTCTCAG | CGCTTTGAGA | CGATTGAGTT | TGATGAGAGT | GCAGGGCAG | TGCTGAGGAT | 300 |
| CCAGCCGCTG | AGGACACCGC | GGGATGAAAA | CGTGTACGAG | TGTGTGGCCC | AGAACTCGGT | 360 |
| TGGGGAGATC | ACAGTCCATG | CCAAGCTTAC | TGTCCTCCGA | GAGGACCAGC | TGCCCTCTGG | 420 |
| CTTCCCCAAC | ATCGACATGG | GCCCACAGTT | GAAGGTGGTG | GAGCGGACAC | GGACAGCCAC | 480 |
| CATGCTCTGT | GCAGCCAGCG | GCAACCCTGA | CCCTGAGATC | ACCTGGTTCA | AGGACTTCCT | 540 |
| GCCTGTGGAT | CCTAGTGCCA | GCAATGGACG | CATCAAACAG | CTGCGATCAG | GAGCCCTGCA | 600 |
| GATTGAAAGC | AGTGAGGAAA | CCGACCAGGG | CAAATATGAG | TGTGTGGCCA | CCAACAGCGC | 660 |
| CGGCGTGCGC | TACTCCTCAC | CTGCCAACCT | CTACGTGCGA | GTCCGCCGCG | TGGCCCCGCG | 720 |
| CTTCTCCATC | CTGCCCATGA | GCCACGAGAT | CATGCCAGGG | GGCAACGTGA | ACATCACCTG | 780 |
| CGTGGCCGTG | GGCTCGCCCA | TGCCATACGT | GAAGTGGATG | CAGGGGCCG | AGGACCTGAC | 840 |
| CCCCGAGGAT | GACATGCCCG | TGGGTCGGAA | CGTGCTGGAA | CTCACAGATG | TCAAGGACTC | 900 |
| GGCCAACTAC | CACCCCTGCG | TGGCCATGTC | CAGCCTGGGC | GTCATTGAGG | CGGTTGCTCA | 960 |
| GATCACGGTG | AAATCTCTCC | CCAAAGCTCC | CGGGACTCCC | ATGGTGACTG | AGAACACAGC | 1020 |
| CACCAGCATC | ACCATCACGT | GGGACTCGGG | CAACCCAGAT | CCTGTGTCCT | ATTACGTCAT | 1080 |
| CGAATATAAA | TCCAAGAGCC | AAGACGGGCC | GTATCAGATT | AAAGAGGACA | TCACCACCAC | 1140 |
| ACGTTACAGC | ATCGGCGGCC | TGAGCCCCAA | CTCGGAGTAC | GAGATCTGGG | TGTCGGCCGT | 1200 |
| CAACTCCATC | GGCCAGGGGC | CCCCCAGCGA | GTCCGTGGTC | ACCCGCACAG | GCGAGCAGGC | 1260 |
| CCCGGCCAGG | CCGCCGCGGA | ACGTGCAAGC | CCGGATGCTC | AGCGCGACCA | CCATGATTGT | 1320 |
| GCAGTGGGAG | GAGCCGGTGG | AGCCCAACGG | CCTGATCCGC | GGCTACCGCG | TCTACTACAC | 1380 |
| CATGGAACCG | GAGCACCCCG | TGGGCAACTG | GCAGAAGCAC | AACGTGGACG | ACAGCCTGCT | 1440 |
| GACCACCGTG | GGCAGCCTGC | TGGAGGACGA | GACCTACACC | GTGCGGGTGC | TCGCCTTCAC | 1500 |
| CTCCGTCGGC | GACGGGCCCC | TCTCGGACCC | CATCCAGGTC | AAGACGCAGC | AGGGAGTGCC | 1560 |
| GGGCCAGCCC | ATGAACCTGC | GGGCCGAGGC | CAGGTCGGAG | ACCAGCATCA | CGCTGTCCTG | 1620 |
| GAGCCCCCG | CGGCAGGAGA | GTATCATCAA | GTACGAGCTC | CTCTTCCGGG | AAGGCGACCA | 1680 |
| TGGCCGGGAG | GTGGGAAGGA | CCTTCGACCC | GACGACTTCC | TACGTGGTGG | AGGACCTGAA | 1740 |
| GCCCAACACG | GAGTACGCCT | TCCGCCTGGC | GGCCCGCTCG | CCGCAGGGCC | TGGGCGCCTT | 1800 |
| CACCCCCGTG | GTGCGGCAGC | GCACGCTGCA | GTCCAAACCG | TCAGCCCCCC | CTCAAGACGT | 1860 |
| TAAATGTGTC | AGCGTGCGCT | CCACGGCCAT | TTTGGTAAGT | TGGCGCCCGC | CGCCGCCGGA | 1920 |
| AACGCACAAC | GGGGCCCTGG | TGGGCTACAG | CGTCCGCTAC | CGACCGCTGG | GCTCAGAGGA | 1980 |
| CCCGGAACCC | AAGGAGGTGA | ACGGCATCCC | CCCGACCACC | ACTCAGATCC | TGCTGGAGGC | 2040 |

```
CTTGGAGAAG  TGGACCCAGT  ACCGCATCAC  GACTGTCGCT  CACACAGAGG  TGGGACCAGG   2100

GCCCGAGAGC  TCGCCCGTGG  TCGTCCGCAC  CGACGAGGAT  GTGCCCAGCG  CGCCGCCGCG   2160

GAAGGTGGAG  GCGGAGGCGC  TCAACGCCAC  GGCCATCCGC  GTGCTGTGGC  GCTCGCCCGC   2220

GCCCGGCCGG  CAGCACGGCC  AGATCCGCGG  CTACCAGGTC  CACTACGTGC  GCATGGAGGG   2280

CGCCGAGGCC  CGCGGGCCGC  CGCGCATCAA  GGACGTCATG  CTGGCCGATG  CCCAGGAGAT   2340

GGTCATCACA  AACTTGCAGC  CTGAGACCGC  GTACTCCATC  ACGGTAGCCG  CCTACACCAT   2400

GAAGGGCGAT  GGCGCTCGCA  GCAAACCCAA  GGTGGTTGTG  ACCAAGGGAG  CAGTGCTGGG   2460

CCGCCCAACC  CTGTCGGTGC  AGCAGACCCC  CGAGGGCAGC  CTGCTGGCAC  GCTGGGAGCC   2520

CCCGGCTGGC  ACCGCGGAGG  ACCAGGTGCT  GGGCTACCGC  CTGCAGTTTG  CCGTGAGGA    2580

CTCGACGCCC  CTGGCCACCC  TGGAGTTCCC  GCCCTCCGAG  GACCGCTACA  CGGCATCAGG   2640

CGTGCACAAG  GGGGCCACGT  ATGTGTTCCG  GCTTGCGGCC  CGGAGCCCGG  GCGGCCTGGG   2700

CGAGGAGGCA  GCCGAGGTCC  TGAGCATCCC  GGAGGACACG  CCCCGTGGCC  ACCCGCAGAT   2760

TCTGGAGGCG  GCCGGCAACG  CCTCGGCCGG  GACCGTCCTT  CTCCGCTGGC  TGCCACCCGT   2820

GCCCGCCGAG  CGCAACGGGG  CCATCGTCAA  ATACACGGTG  CCGTGCGGG   AGGCCGGTGC   2880

CCTGGGCCCT  GCCCGAGAGA  CTGAGCTGCC  GGCAGGCCGG  CTGAGCCGGG  CGCGGAGAAC   2940

GCTCACGCTG  CAGGGCCTGA  AGCCCGACAC  GGCCTATGAC  CTCCAAGTGC  GAGCCCACAC   3000

GCGCCGGGGC  CCTGGCCCCT  TCAGCCCCCC  CGTCCGCTAC  CGGACGTTCC  TGCGGGACCA   3060

AGTCTCGCCC  AAGAACTTCA  AGGTGAAAAT  GATCATGAAG  ACATCAGTTC  TGCTCAGCTG   3120

GGAGTTCCCT  GACAACTACA  ACTCACCCAC  ACCCTACAAG  ATCCAGTACA  ATGGGCTCAC   3180

ACTGGATGTG  GATGGCCGTA  CCACCAAGAA  GCTCATCACG  CACCTCAAGC  CCCACACCTT   3240

CTACAACTTT  GTGCTGACCA  ATCGCGGCAG  CAGCCTGGGC  GGCCTCCAGC  AGACGGTCAC   3300

CGCCTGGACT  GCCTTCAACC  TGCTCAACGG  CAAGCCCAGC  GTCGCCCCA   AGCCTGATGC   3360

TGACGGCTTC  ATCATGGTGT  ATCTTCCTGA  CGGCCAGAGC  CCCGTGCCTG  TCCAGAGCTA   3420

TTTCATTGTG  ATGGTGCCAC  TGCGCAAGTC  TCGTGGAGGC  CAATTCCTGA  CCCCGCTGGG   3480

TAGCCCAGAG  GACATGGATC  TGGAAGAGCT  CATCCAGGAC  ATCTCACGGC  TACAGAGGCG   3540

CAGCCTGCGG  CACTCGCGTC  AGCTGGAGGT  GCCCCGGCCC  TATATTGCAG  CTCGCTTCTC   3600

TGTGCTGCCA  CCCACGTTCC  ATCCCGGCGA  CCAGAAGCAG  TATGGCGGCT  TCGATAACCG   3660

GGGCCTGGAG  CCCGGCCACC  GCTATGTCCT  CTTCGTGCTT  GCCGTGCTTC  AGAAGAGCGA   3720

GCCTACCTTT  GCAGCCAGTC  CCTTCTCAGA  CCCCTTCCAG  CTGGATAACC  CGGACCCCCA   3780

GCCCATCGTG  GATGGCGAGG  AGGGGCTTAT  CTGGGTGATC  GGGCCTGTGC  TGGCCGTGGT   3840

CTTCATAATC  TGCATTGTCA  TTGCTATCCT  GCTCTACAAG  AACAAACCCG  ACAGTAAACG   3900

CAAGGACTCA  GAACCCCGCA  CCAAATGCCT  CCTGAACAAT  GCCGACCTCG  CCCCTCACCA   3960

CCCCAAGGAC  CCTGTGGAAA  TGAGACGCAT  TAACTTCCAG  ACTCCAGGCA  TGCTTAGCCA   4020

CCCGCCAATT  CCCATCGCAG  ACATGGCGGA  GCACACGGAG  CGGCTCAAGG  CCAACGACAG   4080

CCTCAAGCTC  TCCCAGGAGT  ATGAGTCCAT  CGACCCTGGA  CAGCAGTTCA  CATGGGAACA   4140

TTCCAACCTG  GAAGTGAACA  AGCCGAAGAA  CCGCTATGCC  AACGTCATCG  CCTATGACCA   4200

CTCCCGTGTC  ATCCTCCAGC  CCATTGAAGG  CATCATGGGC  AGTGATTACA  TCAATGCCAA   4260

CTACGTGGAC  GGCTACCGGC  GTCAGAACGC  GTACATTGCC  ACGCAGGGGC  CGCTGCCTGA   4320

GACCTTTGGG  GACTTCTGGC  GTATGGTGTG  GGAGCAGCGG  TCGGCGACCA  TCGTCATGAT   4380

GACGCGGCTG  GAGGAGAAGT  CACGGATCAA  GTGTGATCAG  TATTGGCCCA  ACAGAGGCAC   4440
```

| | | | | | |
|---|---|---|---|---|---|
| GGAGACCTAC | GGCTTCATCC | AGGTCACGTT | GCTAGATACC | ATCGAGCTGG | CCACATTCTG | 4500
| CGTCAGGACA | TTCTCTCTGC | ACAAGAATGG | CTCCAGTGAG | AAACGCGAGG | TCCGCCAGTT | 4560
| CCAGTTTACG | GCGTGGCCGG | ACCATGGCGT | GCCCGAATAC | CCAACGCCCT | TCCTGGCTTT | 4620
| CCTGCGGAGA | GTCAAGACCT | GCAACCCACC | AGATGCCGGC | CCCATCGTGG | TTCACTGCAG | 4680
| TGCCGGTGTG | GGCCGCACAG | GCTGCTTTAT | CGTCATCGAC | GCCATGCTTG | AGCGGATCAA | 4740
| GCCAGAGAAG | ACAGTCGATG | TCTATGGCCA | CGTGACGCTC | ATGAGGTCCC | AGCGCAACTA | 4800
| CATGGTGCAG | ACGGAGGACC | AGTACAGCTT | CATCCACGAG | GCCCTGCTGG | AGGCCGTGGG | 4860
| CTGTGGCAAC | ACAGAAGTGC | CCGCACGCAG | CCTCTATGCC | TACATCCAGA | AGCTGGCCCA | 4920
| GGTGGAGCCT | GGCGAACACG | TCACTGGCAT | GGAACTCGAG | TTCAAGCGGC | TGGCTAACTC | 4980
| CAAGGCCCAC | ACGTCACGCT | TCATCAGTGC | CAATCTGCCT | TGTAAGAAGT | TCAAGAACCG | 5040
| CCTGGTGAAC | ATCATGCCCT | ATGAGAGCAC | ACGGGTCTGT | CTGCAACCCA | TCCGGGGTGT | 5100
| GGAGGGCTCT | GACTACATCA | ACGCCAGCTT | CATTGATGGC | TACAGGCAGC | AGAAGGCCTA | 5160
| CATCGCGACA | CAGGGGCCGC | TGGCGGAGAC | CACGGAAGAC | TTCTGGCGCA | TGCTGTGGGA | 5220
| GAACAATTCG | ACGATCGTGG | TGATGCTGAC | CAAGCTGCGG | GAGATGGGCC | GGGAGAAGTG | 5280
| TCACCAGTAC | TGGCCGGCCG | AGCGCTCTGC | CCGCTACCAG | TACTTTGTGG | TAGATCCGAT | 5340
| GGCAGAATAC | AACATGCCTC | AGTATATCCT | GCGAGAGTTC | AAGGTCACAG | ATGCCCGGGA | 5400
| TGGCCAGTCC | CGGACTGTCC | GGCAGTTCCA | GTTCACAGAC | TGGCCGGAAC | AGGGTGTGCC | 5460
| AAAGTCGGGG | GAGGGCTTCA | TCGACTTCAT | TGGCCAAGTG | CATAAGACTA | AGGAGCAGTT | 5520
| TGGCCAGGAC | GGCCCCATCT | CTGTCCACTG | CAGTGCCGGC | GTGGGCAGGA | CGGGCGTCTT | 5580
| CATCACGCTT | AGCATCGTGC | TGGAGCGGAT | GCGGTATGAA | GGCGTGGTGG | ACATCTTTCA | 5640
| GACGGTGAAG | ATGCTACGAA | CCCAGCGGCC | GGCCATGGTG | CAGACAGAGG | ATGAGTACCA | 5700
| GTTCTGTTAC | CAGGCGGCAC | TGGAGTACCT | CGGAAGCTTT | GACCACTATG | CAACCTAAAG | 5760
| CCATGGTCCC | CCCCAGGCCC | GACACCACTG | GCCCCGGATG | CCTCTGCCCC | TCCCGGGCGG | 5820
| ACCTCCTGAG | GCCTGGACCC | CCAGTGGGCA | GGGCAGGAGG | TGGCAGCGGC | AGCAGCTGTG | 5880
| TTTCTGCACC | ATTTCCGAGG | ACGACGCAGC | CCCTCGAGCC | CCCCACCGG | CCCCGGCCGC | 5940
| CCCAGCGACC | TCCCTGGCAC | GGCCGCCGCC | TTCAAATACT | TGGCACATTC | CCCCGAATTC | 6000

( 2 ) INFORMATION FOR SEQ ID NO:7:

( i ) SEQUENCE CHARACTERISTICS:
        ( A ) LENGTH: 699 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Met Glu Pro Phe Cys Pro Leu Leu Leu Ala Ser Phe Ser Leu Ser Leu
 1               5                  10                  15

Ala Arg Ala Gly Gln Gly Asn Asp Thr Thr Pro Thr Glu Ser Asn Trp
            20                  25                  30

Thr Ser Thr Thr Ala Gly Pro Pro Asp Pro Gly Ala Ser Gln Pro Leu
        35                  40                  45

Leu Thr Trp Leu Leu Leu Pro Leu Leu Leu Leu Phe Leu Leu Ala
    50                  55                  60

Ala Tyr Phe Phe Arg Phe Arg Lys Gln Arg Lys Ala Val Val Ser Ser
65                  70                  75                  80
```

-continued

```
Asn  Asp  Lys  Lys  Met  Pro  Asn  Gly  Ile  Leu  Glu  Glu  Gln  Glu  Gln  Gln
               85                      90                          95

Arg  Val  Met  Leu  Leu  Ser  Arg  Ser  Pro  Ser  Gly  Pro  Lys  Lys  Phe  Phe
              100                     105                         110

Pro  Ile  Pro  Val  Glu  His  Leu  Glu  Glu  Glu  Ile  Arg  Val  Arg  Ser  Ala
              115                     120                         125

Asp  Asp  Cys  Lys  Arg  Phe  Arg  Glu  Glu  Phe  Asn  Ser  Leu  Pro  Ser  Gly
         130                     135                         140

His  Ile  Gln  Gly  Thr  Phe  Glu  Leu  Ala  Asn  Lys  Glu  Glu  Asn  Arg  Glu
145                          150                     155                     160

Lys  Asn  Arg  Tyr  Pro  Asn  Ile  Leu  Pro  Asn  Asp  His  Cys  Arg  Val  Ile
              165                     170                         175

Leu  Ser  Gln  Val  Asp  Gly  Ile  Pro  Cys  Ser  Asp  Tyr  Ile  Asn  Ala  Ser
              180                     185                         190

Tyr  Ile  Asp  Gly  Tyr  Lys  Glu  Lys  Asn  Lys  Phe  Ile  Ala  Ala  Gln  Gly
         195                     200                         205

Pro  Lys  Gln  Glu  Thr  Val  Asn  Asp  Phe  Trp  Arg  Met  Val  Trp  Glu  Gln
     210                          215                     220

Arg  Ser  Ala  Thr  Ile  Val  Met  Leu  Thr  Asn  Leu  Lys  Glu  Arg  Lys  Glu
225                          230                     235                     240

Glu  Lys  Cys  Tyr  Gln  Tyr  Trp  Pro  Asp  Gln  Gly  Cys  Trp  Thr  Tyr  Gly
              245                     250                         255

Asn  Ile  Arg  Val  Cys  Val  Glu  Asp  Cys  Val  Val  Leu  Val  Asp  Tyr  Thr
              260                     265                         270

Ile  Arg  Lys  Phe  Cys  Ile  His  Pro  Gln  Leu  Pro  Asp  Ser  Cys  Lys  Ala
          275                     280                         285

Pro  Arg  Leu  Val  Ser  Gln  Leu  His  Phe  Thr  Ser  Trp  Pro  Asp  Phe  Gly
     290                          295                     300

Val  Pro  Phe  Thr  Pro  Ile  Gly  Met  Leu  Lys  Phe  Leu  Lys  Lys  Val  Lys
305                          310                     315                     320

Thr  Leu  Asn  Pro  Ser  His  Ala  Gly  Pro  Ile  Val  His  Cys  Ser  Ala
                   325                     330                         335

Gly  Val  Gly  Arg  Thr  Gly  Thr  Phe  Ile  Val  Ile  Asp  Ala  Met  Met  Asp
               340                     345                         350

Met  Ile  His  Ser  Glu  Gln  Lys  Val  Asp  Val  Phe  Glu  Phe  Val  Ser  Arg
              355                     360                         365

Ile  Arg  Asn  Gln  Arg  Pro  Gln  Met  Val  Gln  Thr  Asp  Val  Gln  Tyr  Thr
     370                          375                     380

Phe  Ile  Tyr  Gln  Ala  Leu  Leu  Glu  Tyr  Tyr  Leu  Tyr  Gly  Asp  Thr  Glu
385                          390                     395                     400

Leu  Asp  Val  Ser  Ser  Leu  Glu  Arg  His  Leu  Gln  Thr  Leu  His  Ser  Thr
                    405                     410                         415

Ala  Thr  His  Phe  Asp  Lys  Ile  Gly  Leu  Glu  Glu  Glu  Phe  Arg  Lys  Leu
               420                     425                         430

Thr  Asn  Val  Arg  Ile  Met  Lys  Glu  Asn  Met  Arg  Thr  Gly  Asn  Leu  Pro
              435                     440                         445

Ala  Asn  Met  Lys  Lys  Ala  Arg  Val  Ile  Gln  Ile  Ile  Pro  Tyr  Asp  Phe
     450                          455                     460

Asn  Arg  Val  Ile  Leu  Ser  Met  Lys  Arg  Gly  Gln  Glu  Phe  Thr  Asp  Tyr
465                          470                     475                     480

Ile  Asn  Ala  Ser  Phe  Ile  Asp  Gly  Tyr  Arg  Gln  Lys  Asp  Tyr  Phe  Met
                    485                     490                         495

Ala  Thr  Gln  Gly  Pro  Leu  Ala  His  Thr  Val  Glu  Asp  Phe  Trp  Arg  Met
```

|   |   |   | 500 |   |   |   |   |   |   |   | 505 |   |   |   |   |   |   |   | 510 |   |   |
|---|---|---|---|---|---|---|---|---|---|---|---|---|---|---|---|---|---|---|---|---|---|
| Val | Trp | Glu<br>515 | Trp | Lys | Ser | His | Thr<br>520 | Ile | Val | Met | Leu | Thr<br>525 | Glu | Val | Gln |
| Glu | Arg<br>530 | Glu | Gln | Asp | Lys | Cys<br>535 | Tyr | Gln | Tyr | Trp | Pro<br>540 | Thr | Glu | Gly | Ser |
| Val<br>545 | Thr | His | Gly | Asp | Ile<br>550 | Thr | Ile | Glu | Ile | Lys<br>555 | Ser | Asp | Thr | Leu | Ser<br>560 |
| Glu | Ala | Ile | Ser | Val<br>565 | Arg | Asp | Phe | Leu | Val<br>570 | Thr | Phe | Lys | Gln | Pro<br>575 | Leu |
| Ala | Arg | Gln | Glu<br>580 | Glu | Gln | Val | Arg | Met<br>585 | Val | Arg | Gln | Phe | His<br>590 | Phe | His |
| Gly | Trp | Pro<br>595 | Glu | Val | Gly | Ile | Pro<br>600 | Ala | Glu | Gly | Lys | Gly<br>605 | Met | Ile | Asp |
| Leu | Ile<br>610 | Ala | Ala | Val | Gln | Lys<br>615 | Gln | Gln | Gln | Gln | Thr<br>620 | Gly | Asn | His | Pro |
| Ile<br>625 | Thr | Val | His | Cys | Ser<br>630 | Ala | Gly | Ala | Gly | Arg<br>635 | Thr | Gly | Thr | Phe | Ile<br>640 |
| Ala | Leu | Ser | Asn | Ile<br>645 | Leu | Glu | Arg | Val | Lys<br>650 | Ala | Glu | Gly | Leu | Leu<br>655 | Asp |
| Val | Phe | Gln | Ala<br>660 | Val | Lys | Ser | Leu | Arg<br>665 | Leu | Gln | Arg | Pro | His<br>670 | Met | Val |
| Gln | Thr | Leu<br>675 | Glu | Gln | Tyr | Glu | Phe<br>680 | Cys | Tyr | Lys | Val | Val<br>685 | Gln | Asp | Phe |
| Ile | Asp<br>690 | Ile | Phe | Ser | Asp | Tyr<br>695 | Ala | Asn | Phe | Lys |

What is claimed is:

1. A purified human PTP-OB protein which comprises the amino acid sequence set forth in SEQ ID NO:5.

2. A purified human PTP-OB protein of claim 1 obtained by culturing a recombinant host cell transfected or transformed with a nucleic acid vector which expresses the PTP-OB protein as set forth in SEQ ID NO:5 and recovering the PTP-OB protein.

3. A purified polypeptide which comprises amino acid 1285 to amino acid 1911 as set forth in SEQ ID NO:5.

4. A purified polypeptide of claim 3 obtained by culturing a recombinant host cell transfected or transformed with a nucleic acid vector which expresses the polypeptide comprising amino acid 1285 to amino acid 1911 as set forth in SEQ ID NO:5 and recovering the polypeptide.

5. A purified polypeptide of claim 3 wherein said polypeptide further comprises glutathione S-transferase (GST).

6. A purified human PTP-OB protein which consists of the amino acid sequence set forth in SEQ ID NO:5.

7. A purified human PTP-OB protein of claim 6 obtained by culturing a recombinant host cell transfected or transformed with a nucleic acid vector which expresses the PTP-OB protein as set forth in SEQ ID NO:5 and recovering the PTP-OB protein.

* * * * *